United States Patent [19]
Harada et al.

[11] Patent Number: 5,653,241
[45] Date of Patent: Aug. 5, 1997

[54] BLOOD-PRESSURE MONITOR APPARATUS

[75] Inventors: Chikao Harada; Yoshihisa Miwa, both of Komaki, Japan

[73] Assignee: Colin Corporation, Aichi, Japan

[21] Appl. No.: 517,237

[22] Filed: Aug. 21, 1995

[30]      Foreign Application Priority Data

Aug. 23, 1994  [JP]  Japan .................................. 6-198117
Jan. 7, 1995   [JP]  Japan .................................. 7-004802

[51] Int. Cl.⁶ .................................................. A61B 5/02
[52] U.S. Cl. ............................................ 128/681; 128/683
[58] Field of Search ................................... 128/680, 681, 128/682, 683, 687

[56]              References Cited

U.S. PATENT DOCUMENTS

| 4,729,383 | 3/1988  | Susi ...................... | 128/680 |
| 4,774,960 | 10/1988 | Arnold et al. ........... | 128/681 |
| 5,243,990 | 9/1993  | Aung et al. ............. | 128/680 |
| 5,279,303 | 1/1994  | Kawamura et al. .      |         |
| 5,316,006 | 5/1994  | Inage et al. ............ | 128/680 |
| 5,404,878 | 4/1995  | Frankenreiter et al. .. | 128/680 |

FOREIGN PATENT DOCUMENTS

| 0 510 720  | 10/1992 | European Pat. Off. . |
| 60-241422  | 11/1985 | Japan . |
| 61-103432  | 5/1986  | Japan . |
| 4-367647   | 12/1992 | Japan . |
| WO-A-88 03003 | 5/1988 | WIPO . |

*Primary Examiner*—Lee S. Cohen
*Assistant Examiner*—Eric F. Winakur
*Attorney, Agent, or Firm*—Oliff & Berridge

[57]              ABSTRACT

A blood pressure monitor apparatus for monitoring a blood pressure of a living subject, including a blood-pressure measuring device which includes an inflatable cuff adapted to be wound around a body portion of a living subject and measures a blood pressure of the subject by changing a pressing pressure of the cuff to not lower than a systolic blood pressure of the subject, a cuff-pressure control device which iteratively changes, after a predetermined rest period following the blood pressure measurement of the blood-pressure measuring device, the pressure of the cuff to a predetermined value lower than the systolic blood pressure of the subject, and a blood-pressure-change identifying device for identifying a change of the blood pressure of the subject based on (a) respective amplitudes of first heartbeat-synchronous pulses obtained from the cuff during the blood pressure measurement of the blood-pressure measuring device, (b) respective pressures of the cuff when the first pulses are obtained, (c) respective amplitudes of second heartbeat-synchronous pulses obtained from the cuff during each of the iterative changings of the cuff pressure by the cuff-pressure control device, and (d) respective pressures of the cuff when the second pulses are obtained.

21 Claims, 25 Drawing Sheets

BLOOD-PRESSURE MONITOR APPARATUS

BACKGROUND OF THE INVENTION

1. Field of the Invention

The present invention relates to a blood-pressure monitor apparatus which monitors the blood pressure of a living subject.

2. Related Art Statement

The blood pressure of a living subject such as a patient may continuously be monitored by using an automatic blood-pressure (BP) measuring device including an inflatable cuff adapted to be wound around a body portion (e.g., upper arm) of the subject. In this case, the BP measuring device periodically carries out BP measuring operations at a regular interval of time. However, if this interval is shortened to improve the reliability of the BP monitoring, then the frequency of pressing of the cuff against the subject's body portion increases, thereby causing the subject to feel even serious discomfort.

In contrast, a different BP monitoring method is disclosed in Japanese Patent Applications laid open for inspection under Publication Nos. 61-103432 and 60-241422. In this method, an inflatable cuff is wound around a body portion of a living subject and is inflated to apply an appropriate pressing pressure to the body portion, and a pulse-wave sensor continuously detects heartbeat-synchronous pulses produced as pressure oscillations in the cuff. The disclosed BP monitor device continuously estimates the BP values of the subject based on the respective amplitudes of the continuous pulses.

However, in the above-described BP monitor device, the pressing pressure of the cuff cannot be decreased to sufficiently low levels to be able to reduce the physical and/or psychological load to the subject, because the changing of the pulse amplitudes at such low levels does not accurately correspond to the changing of the subject's blood pressure. A curve indicated at solid line in FIG. 35 represents the envelope of the pulse amplitudes which are obtained from the cuff as the cuff pressure Pc is changed. If the blood pressure of the subject decreases from a normal level represented by the solid-line curve, the solid-line curve is changed into a curve indicated at one-dot chain line in the same graph. In the case where the pulse amplitudes are detected at a low cuff pressure, $P_K$, the amount of changing of the pulse amplitudes is significantly smaller than that of the subject's blood pressure, thereby lowering the accuracy of monitoring of the prior BP monitor device.

SUMMARY OF THE INVENTION

It is therefore an object of the present invention to provide a blood-pressure monitor apparatus which monitors the blood pressure of a living subject with high accuracy and without causing the subject to feel discomfort.

The above object has been achieved by the present invention, which provides a blood pressure monitor apparatus for monitoring a blood pressure of a living subject, comprising a blood-pressure measuring device which includes an inflatable cuff adapted to be wound around a body portion of a living subject and measures a blood pressure of the subject by changing a pressing pressure of the cuff to not lower than a systolic blood pressure of the subject, a cuff-pressure control device which iteratively changes, after a predetermined rest period following the blood pressure measurement of the blood-pressure measuring device, the pressure of the cuff to a predetermined value lower than the systolic blood pressure of the subject, and blood-pressure-change identifying means for identifying a change of the blood pressure of the subject based on (a) respective amplitudes of first heartbeat-synchronous pulses obtained from the cuff during the blood pressure measurement of the blood-pressure measuring device, (b) respective pressures of the cuff when the first pulses are obtained, (c) respective amplitudes of second heartbeat-synchronous pulses obtained from the cuff during each of the iterative changings of the cuff pressure by the cuff-pressure control device, and (d) respective pressures of the cuff when the second pulses are obtained.

The blood-pressure monitor apparatus constructed as described above monitors the blood pressure of the subject with high accuracy, because the apparatus utilizes both the pulse amplitudes and corresponding cuff pressures obtained in the BP measurement of the BP measuring device and the pulse amplitudes and corresponding cuff pressures obtained during each cuff-pressure changing of the cuff-pressure control device. In addition, since the present monitor apparatus monitors the subject's blood pressure by iteratively changing the cuff pressure within a low pressure range between the atmospheric pressure and the predetermined pressure value lower than the subject's systolic blood pressure, the monitor apparatus does not cause the subject to feel serious discomfort.

In a preferred embodiment of the present invention, the blood pressure monitor apparatus further comprises a first memory which stores the respective amplitudes of the first pulses obtained from the cuff during the blood pressure measurement of the blood-pressure measuring device, and the respective pressures of the cuff when the first pulses are obtained, and a second memory which stores the respective amplitudes of the second pulses obtained from the cuff during the each of the iterative changings of the cuff pressure by the cuff-pressure control device, and the respective pressures of the cuff when the second pulses are obtained.

In another embodiment of the present invention, the blood-pressure-change identifying means comprises cuff-pressure comparing means for comparing a first pressure of the cuff at which one of the first pulses which has a greatest amplitude of the first pulses obtained when the pressures of the cuff are not higher than the predetermined value is obtained, with a second pressure of the cuff at which one of the second pulses which has a greatest amplitude is obtained, and means for identifying the change of the blood pressure of the subject, when the cuff-pressure comparing means provides a first comparison result that the second cuff pressure is lower than the first cuff pressure.

In another embodiment of the present invention, the blood-pressure-change identifying means comprises cuff-pressure comparing means for comparing a first pressure of the cuff at which one of the first pulses which has a greatest amplitude of the first pulses obtained when the pressures of the cuff are not higher than the predetermined value is obtained, with a second pressure of the cuff at which one of the second pulses which has a greatest amplitude is obtained, judging means for judging, when the cuff-pressure comparing means provides a second comparison result that the second cuff pressure is not lower than the first cuff pressure, whether an amplitude of the second pulses which corresponds to a reference cuff-pressure value has changed from an amplitude of the first pulses which corresponds to the reference cuff-pressure value, by not smaller than a predetermined proportion of the amplitude of the first pulses, and means for identifying the change of the blood pressure of the subject when the judging means makes a positive judgment.

In this embodiment, the judging means may comprise means for judging whether the amplitude of the second pulses obtained as a value of an envelope or a cumulative curve of the second pulses which value corresponds to the reference cuff-pressure value has changed from the amplitude of the first pulses obtained as a value of an envelope or a cumulative curve of the first pulses which value corresponds to the reference cuff-pressure value.

In another embodiment of the present invention, the blood-pressure-change identifying means comprises rate-of-change calculating means for calculating a first rate of change of the respective amplitudes of the first pulses obtained when the pressures of the cuff are not higher than the predetermined value, with respect to the corresponding pressures of the cuff, and a second rate of change of the respective amplitudes of the second pulses with respect to the respective pressures of the cuff when the second pulses are obtained, and means for identifying the change of the blood pressure of the subject when a difference between the first and second rates of change is greater than a predetermined value.

In another embodiment of the present invention, the blood pressure monitor apparatus further comprises a first pulse-rate measuring device which measures a first pulse rate of the subject during the blood pressure measurement of the blood-pressure measuring device, and a second pulse-rate measuring device which measures a second pulse rate of the subject during the each of the iterative changings of the cuff pressure by the cuff-pressure control device, the blood-pressure-change identifying means identifying the change of the blood pressure of the subject when the second pulse rate has changed from the first pulse rate by not smaller than a predetermined amount.

In another embodiment of the present invention, the cuff-pressure control device comprises means for iteratively changing, after the predetermined rest period, the pressure of the cuff to the predetermined value not higher than a mean blood pressure of the subject, and the blood-pressure-change identifying means comprises means for identifying the change of the blood pressure of the subject based on a first relationship between the respective amplitudes of the first pulses and the respective pressures of the cuff when the first pulses are obtained and a second relationship between the respective amplitudes of the second pulses and the respective pressures of the cuff when the second pulses are obtained. The present monitor apparatus monitors the blood pressure of the subject with .higher accuracy, because the apparatus identifies a change of the subject's blood pressure based on both the first relationship between the pulse amplitudes and corresponding cuff pressures obtained in the BP measurement of the BP measuring device and the second relationship between the pulse amplitudes and corresponding cuff pressures obtained during each cuff-pressure changing of the cuff-pressure control device. In addition, since the monitor apparatus monitors the subject's blood pressure by iteratively changing the cuff pressure within a low pressure range between the atmospheric pressure and the predetermined pressure value lower than the subject's mean blood pressure, the apparatus more effectively prevents the subject from feeling discomfort.

In another embodiment of the present invention, the blood-pressure-change identifying means comprises pulse-amplitude-window determining means for determining, in a coordinate system defined by a first axis indicative of the cuff pressure and a second axis indicative of the pulse amplitude, a pulse-amplitude window which is defined by a reference line representing the first relationship and has a first width along the second axis, deviation identifying means for counting, from data points plotted in the coordinate system which points represent, as the second relationship, the respective amplitudes of the second pulses and the respective pressures of the cuff when the second pulses are obtained, a first number of the data points which fall within the pulse-amplitude window, and identifying a deviation of the second relationship from the first relationship based on the counted first number, and means for identifying the change of the blood pressure of the subject when the deviation identifying means identifies the deviation of the second relationship from the first relationship. In this embodiment, a change of the subject's blood pressure is identified based on a deviation of the pulse amplitudes of the second relationship from those of the first relationship.

According to a preferred feature of the present invention, the blood-pressure-change identifying means further comprises .cuff-pressure window determining means for determining, in the coordinate system, a cuff-pressure window which is defined by the reference line and has a second width along the first axis, the deviation identifying means counting, from the data points plotted in the coordinate system, a second number of the data points which fall within the cuff-pressure window, and identifying a deviation of the second relationship from the first relationship based on both the counted first number and the counted second number, the blood-pressure-change identifying means comprising means for identifying the change of the blood pressure of the subject when the deviation identifying means identifies the deviation of the second relationship from the first relationship based on both the first and second counted numbers. In this case, a change of the subject's blood pressure is identified based on both a deviation of the pulse amplitudes of the second relationship from those of the first relationship and a deviation of the pressures of the second relationship from those of the first relationship.

According to another feature of the present invention, the the pulse-amplitude window determining means comprises approximate-line determining means for determining, as the reference line, an approximate line approximating the first relationship within a range of the pressures of the cuff which are not higher than the mean blood pressure of the subject, and means for determining the pulse-amplitude window which has the approximate line as a center line thereof and respective halves of the first width on both sides of the approximate line. In this case, the approximate-line determining means may comprise means for determining, as the approximate line, at least one of (a) a least-square approximate line and (b) a regression line, based on data points plotted in the coordinate system which points represent, as the first relationship, the respective amplitudes of the first pulses and the respective pressures of the cuff when the first pulses are obtained.

According to another feature of the present invention, the cuff-pressure window determining means comprises approximate-line determining means for determining, as the reference line, an approximate line approximating the first relationship within a range of the pressures of the cuff which are not higher than the mean blood pressure of the subject, and means for determining the cuff-pressure window which has the approximate line as a center line thereof and respective halves of the second width on both sides of the approximate line. In this case, the approximate-line determining means comprises means for determining, as the approximate line, at least one of (a) a least-square approximate line and (b) a regression line, based on data points plotted in the coordinate system which points represent, as the first relationship, the respective amplitudes of the first pulses and the respective pressures of the cuff when the first pulses are obtained.

In another embodiment of the present invention, the blood-pressure-change identifying means comprises area calculating means for calculating an area bounded by a first line representing the first relationship and a second line representing the second relationship, within a predetermined range of the pressures of the cuff, deviation identifying means for identifying a deviation of the second relationship from the first relationship based on the calculated area, and means for identifying the change of the blood pressure of the subject when the deviation identifying means identifies the deviation of the second relationship from the first relationship. In this embodiment, a change of the subject's blood pressure is identified based on a deviation of the pulse amplitudes of the second relationship from those of the first relationship.

According to a preferred feature of the present invention, the area calculating means comprises means for calculating a first area bounded by a first portion of the first line and a first portion of the second line which is greater than the first portion of the first line with respect to the pulse amplitude, and a second area bounded by a second portion of the first line and a second portion of the second line which is smaller than the second portion of the first line with respect to the pulse amplitude, and wherein the blood-pressure-change identifying means comprises means for identifying a decrease of the blood pressure of the subject when the first area is greater than the second area. In this embodiment, a change of the subject's blood pressure, more particularly, a decrease of the same is identified.

According to another feature of the present invention, the area calculating means comprises means for calculating a first area bounded by a first portion of the first line and a first portion of the second line which is greater than the first portion of the first line with respect to the pulse amplitude, and a second area bounded by a second portion of the first line and a second portion of the second line which is smaller than the second portion of the first line with respect to the pulse amplitude, and wherein the blood-pressure-change identifying means comprises means for identifying an increase of the blood pressure of the subject when the second area is greater than the first area. In this embodiment, a change of the subject's blood pressure, more particularly, an increase of the same is identified.

According to another feature of the present invention, the blood pressure monitor apparatus further comprising a blood-pressure re-measuring device which immediately measures a new blood pressure of the subject when the blood-pressure-change identifying means identifies the change of the blood pressure of the subject.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
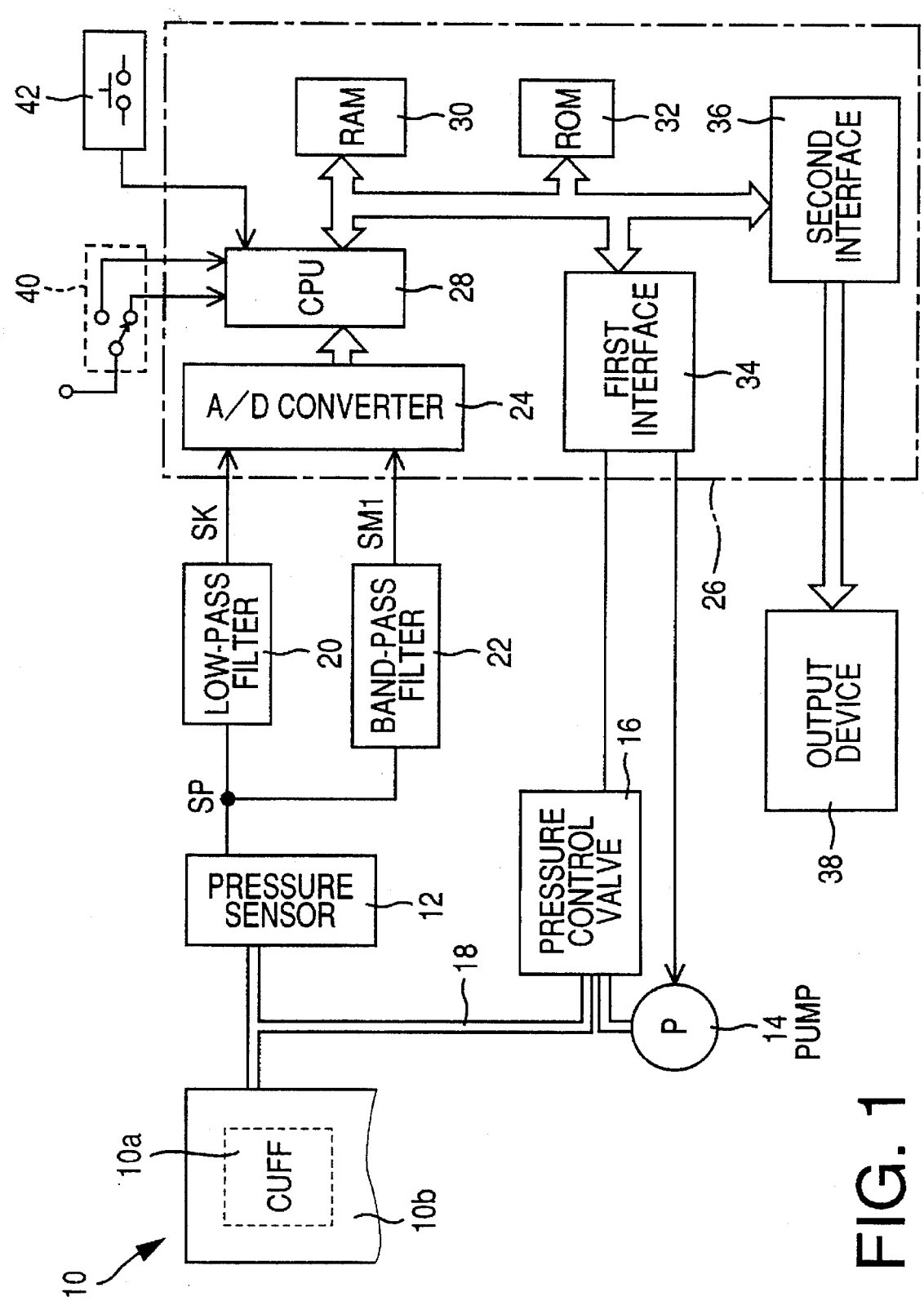
FIG. 1 is a diagrammatic view for illustrating an electrical construction of a blood-pressure monitor apparatus embodying the present invention.

Referring first to FIG. 1, there is shown a blood pressure monitor apparatus embodying the present invention (hereinafter, referred to as the "BP monitor").

In FIG. 1, reference numeral 10 designates an inflatable cuff 10 adapted to be wound around, e.g., an upper arm of a living subject, such as a patient, so as to press the arm. The cuff 10 includes an inflatable bag 10a formed of an elastic sheet such as a rubber sheet or a vinyl sheet. The inflatable bag 10a is accommodated in an arm belt 10b formed of a non-stretchable sheet. The bag 10a of the Cuff 10 is connected to a pressure sensor 12, an air pump 14, and a pressure control valve 16 via air piping 18. The pressure control valve 16 controls the pressing pressure (i.e., air pressure) of the cuff 10 applied to the upper arm of the subject. The control valve 16 provides part of a cuff-pressure control device 56 which will be described later.

The pressure sensor 12 includes a semiconductor pressure-sensing element, detects the air pressure in the cuff 10, and supplies a pressure signal, SP, representative of the detected cuff pressure, to a low-pass filter 20 and a band-pass filter 22. The low-pass filter 20 permits only a direct-current component of the pressure signal SP to pass therethrough, thereby supplying a cuff-pressure signal, SK, representative of a cuff pressure (i.e., static pressure), Pc, to an analog-to-digital (A/D) converter 24. The low-pass filter provides part of a cuff-pressure detecting device 50 which will be described later.

The band-pass filter 22 permits only a 1 to 10 Hz frequency-band component of the pressure signal SP, thereby supplying, to the A/D converter 24, a pulse-wave signal, SM1, representative of a pulse wave containing heartbeat-synchronous pulses that are pressure oscillations or changes produced in the cuff 10 because of pulsation of the arterial vessels running in the subject's arm. The band-pass filter 22 has a narrow frequency-band characteristic to extract, from the pressure signal SP, pulse amplitudes, i.e., pressure oscillations produced in the cuff 10 in synchronism with subject's heartbeats while the cuff pressure is slowly changed (e.g., decreased) at, e.g., 2 to 3 mmHg/sec. Thus, the extracted pulse-wave signal SM1 is free from noise such as motion-related artifact noise. The A/D converter 24 includes a multiplexer for concurrently dealing with the two input signals, SK and SM1, by time sharing. The band-pass filter 22 provides part of a pulse-wave detecting device 52 which will be described later.

The present BP monitor has a control device 26 which is provided by a microcomputer including a central processing unit (CPU) 28, a random access memory (RAM) 30, a read only memory (ROM) 32, a first output interface 34, and a second output interface 36. The CPU 28 processes the signals received from the A/D converter 24, by utilizing a temporary-storage function of the RAM 30, according to a control program pre-stored in the ROM 32. In addition, the CPU 28 drives and controls the air pump 14 and the pressure control valve 16 via the first interface 34, and drives and controls an output device 38 via the second interface 36. The output device 38 includes a display panel for displaying an image which consists of a multiplicity of picture elements and represents numerals and/or waveforms, and a printer for recording the image with an ink on a recording sheet.

A mode-selection switch 40 is operable for switching the BP monitor between a single-measurement mode and a continuous-monitor mode. The mode switch 40 supplies, to the CPU 40, a mode signal representing a selected mode. A start/stop switch 42 is provided to alternately supply, to the CPU 28, an ON signal to start the BP monitor and an OFF signal to stop the same, each time the switch 42 is operated.

Figure 2:
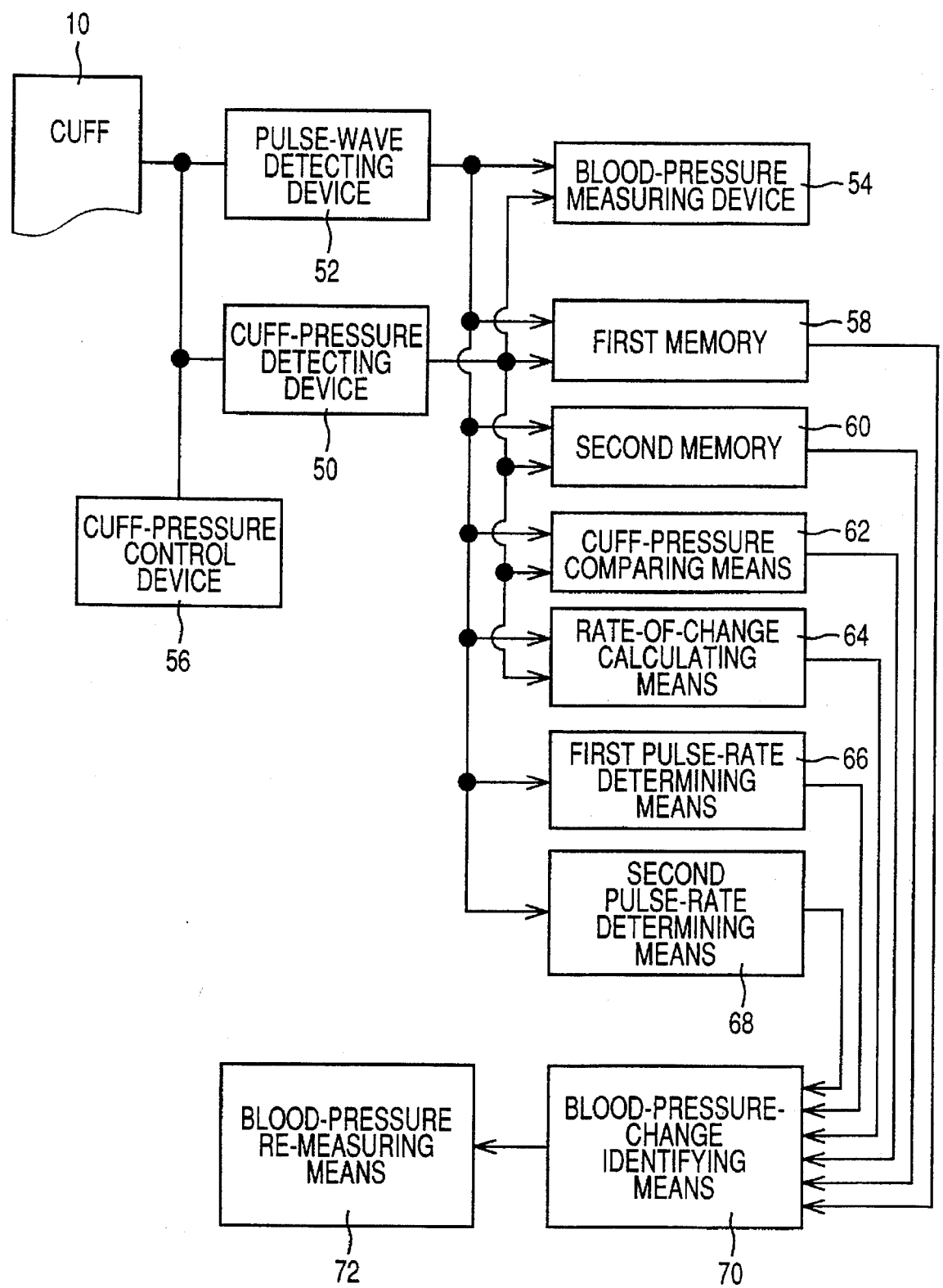
FIG. 2 is a diagrammatic view for illustrating various functions of a control device of the apparatus of FIG. 1.

FIG. 2 illustrates various functions of the control device 26 of the BP monitor. The BP monitor includes an oscillometric blood-pressure (BP) measuring device 54 which determines two cuff pressures at which the rate of change of the pulse amplitudes obtained during the changing of the cuff pressure becomes maximal, as a systolic ($P_{SYS}$) and a diastolic ($P_{DIA}$) blood pressure of the subject, and determines a cuff pressure at which the greatest pulse amplitude is obtained, as a mean ($P_{MEAN}$) blood pressure of the subject. The BP measuring device 54 carries out a BP measurement not only when the start/stop switch 42 is operated to start the BP monitor with the mode switch 40 being placed in the monitor mode, but also when a blood-pressure-change identifying means 70 identifies that the blood pressure of the subject has abnormally changed, as described later. Thus, the BP measuring device 54 also functions as a BP re-measuring device 72.

Figure 3:
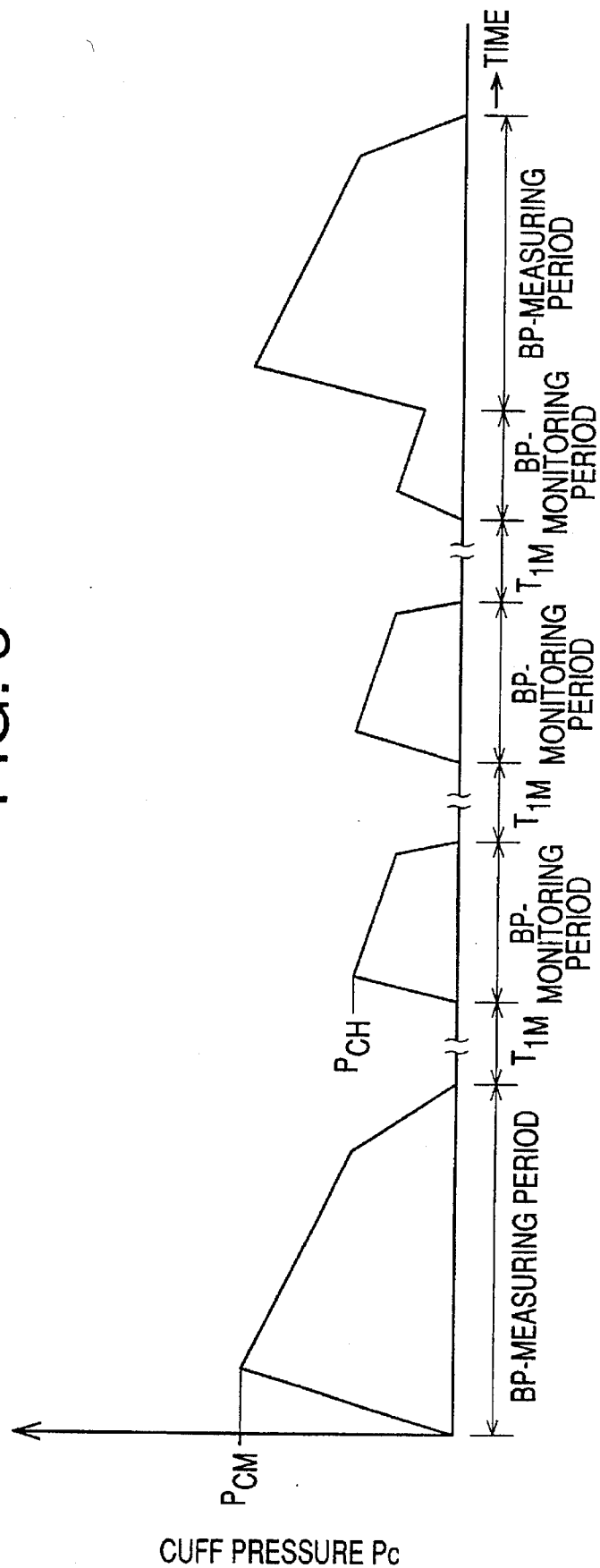
FIG. 3 is a time chart showing the time-wise change of cuff pressure Pc controlled by the control device of FIG. 1.

As shown in FIG. 3, in a BP-measuring period of the BP measuring device 54, the cuff-pressure control device 56 quickly increases the pressing pressure Pc of the cuff 10 to a target pressure, $P_{CM}$, which is pre-determined to be higher than a systolic blood pressure of the subject, and subsequently slowly decreases the cuff pressure Pc at 2 to 3 mmHg/sec. In a non-measurement period in which the BP measuring device 54 does not work, the cuff-pressure control device 56 iteratively increases and decreases the cuff pressure Pc to and from a predetermined pressure value, $P_{CH}$, which is pre-determined to be not higher than a diastolic blood pressure of the subject, while inserting a predetermined rest period between successive two BP-monitoring periods.

A first memory 58 stores the respective amplitudes of heartbeat-synchronous pulses, $Am_s$ ($s=1, 2, 3, \ldots, j$), produced as pressure oscillations in the cuff 10 while the cuff pressure Pc is slowly changed by the BP measuring device 54 in a BP-measuring period. The first memory 58 also stores the cuff pressures, $Pm_s$ ($s=1, 2, 3, \ldots, j$), detected by the cuff-pressure detecting device 50 when the corresponding pulse amplitudes $Am_s$ are detected by the pulse-wave detecting device 52. A second memory 60 stores the respective amplitudes of heartbeat-synchronous pulses, $Am_m$ ($m=1, 2, 3, \ldots, k$), detected by the pulse-wave detecting device 52 while the cuff pressure Pc is slowly changed by the cuff-pressure control device 56 in each BP-monitoring period subsequent to a BP-measuring period, and also stores the cuff pressures, $Pm_m$ ($m=1, 2, 3, \ldots, k$), detected by the cuff-pressure detecting device 50 when the corresponding pulse amplitudes $Am_m$ are detected.

A cuff-pressure comparing means 62 compares a cuff pressure, $Pm_{smax}$, at which a pulse having the greatest or maximum amplitude, $Am_{smax}$, out of the pulses obtained and stored in the first memory 58 when the cuff pressures Pc are not higher than the predetermined value $P_{CH}$ is obtained, with a cuff pressure at which a pulse having the greatest or maximum amplitude, $Am_{mmax}$, out of all the pulses stored in the second memory 60 is obtained. A rate-of-change calculating means 64 calculates a rate of change, $K_s$, of the respective pulse amplitudes $Am_s$ detected and stored in the first memory 58 when the cuff pressure Pc is not higher than the predetermined value $P_{CH}$, with respect to the corresponding cuff pressures $Pm_s$ stored in the same memory 58, and a rate of change, $K_m$, of the respective pulse amplitudes $Am_m$ stored in the second memory 60 with respect to the corresponding cuff pressures $Pm_m$ stored in the same memory 60. The rate of change $K_s$ is defined as the slope of an approximate line, such as a least-square approximate line or a regression line, which is determined based on the data points plotted in a two-dimensional coordinate system having an axis of abscissa indicative of the cuff pressure Pc and an axis of ordinate indicative of the pulse amplitude. Those data points or the approximate line represents a relationship between the pulse amplitudes $Am_s$ and cuff pressures $Pm_s$ detected and stored in the first memory 58 when the cuff pressure Pc is not higher than the predetermined value $P_{CH}$. Similarly, the rate of change $K_m$ is defined as the slope of an approximate line which is determined based on the data points plotted in the same coordinate system, and those data points or the approximate line represents a relationship between the pulse amplitudes $Am_m$ and cuff pressures $Pm_m$ stored in the second memory 60.

A first pulse-rate determining means 66 determines and stores a pulse rate, $PR_s$, of the subject based on the pulses obtained in a BP-measuring period, and a second pulse-rate determining means 68 determines and stores a pulse rate, $PR_m$, of the subject based on the pulses obtained in each of BP-monitoring periods following a BP-measuring period.

The BP-change identifying means 70 identifies a change of the blood pressure of the subject, (a) when the cuff-pressure comparing means 62 provides a comparison result that the cuff pressure $Pm_{mmax}$ is lower than the cuff pressure $Pm_{smax}$, (b) when the cuff-pressure comparing means 62 provides a comparison result that the cuff pressure $Pm_{mmax}$ is not lower than the cuff pressure $Pm_{smax}$, and simultaneously when a pulse amplitude, $M_s$, which is obtained and stored in the first memory 58 when the cuff pressure Pc takes a reference value has changed from a pulse amplitude, $M_m$, which is obtained and stored in the second memory 60 when the cuff pressure Pc takes the reference value, by not smaller than a predetermined proportion of the pulse amplitude $M_s$, (c) when the difference between the two rates of change $K_s$, $K_m$ is greater than a predetermined value, or (d) when the pulse rate $PR_m$ has changed from the pulse rate $PR_s$ by not smaller than a predetermined amount. The pulse amplitude $M_s$ may be obtained as the value of an envelope or a cumulative curve of the pulse amplitudes $Am_s$ stored in the first memory 58, which value corresponds to the reference value of the cuff pressure Pc, and the pulse amplitude $M_m$ may be obtained as the value of an envelope or a cumulative curve of the pulse amplitudes $Am_m$ stored in the second memory 60, which value corresponds to the reference value of the cuff pressure Pc. The BP-change identifying means 70 obtains, from the above-described various identification or judgment results, change evaluation values, $D_1$, $D_2$, $U_1$, $U_2$, H, and a non-change evaluation value, I, which will be described later, and carries out an overall BP-change evaluation, based on those evaluation values, according to the following expression (1):

$$S=k_1 \cdot H \sqrt{[k_2 \cdot U_1 + k_3 \cdot U_2 - (k_4 \cdot D_1 + k_5 \cdot D_2)]} / k_6 \cdot I \quad (1)$$

where $k_1$, $k_2$, $k_3$, $k_4$, $k_5$, and $k_6$ are predetermined constants.

When the overall evaluation value S does not fall within a reference range, the BP-change identifying means 70 identifies or judges that the blood pressure of the subject has changed abnormally, and the BP re-measuring device 72 immediately starts a BP measuring period to carry out a BP measurement on the subject. Thus, the output device 38 displays and/or records the subject's BP values measured immediately after the abnormal BP change.

Next, there will be described the operation of the control device 26 of the BP monitor by reference to the flow chart of FIG. 4 which represents the control program pre-stored in the ROM 32, and the flow chart of FIG. 5 which describes Step S9 of FIG. 4, i.e., abnormal BP-change identifying routine.

Figure 4:
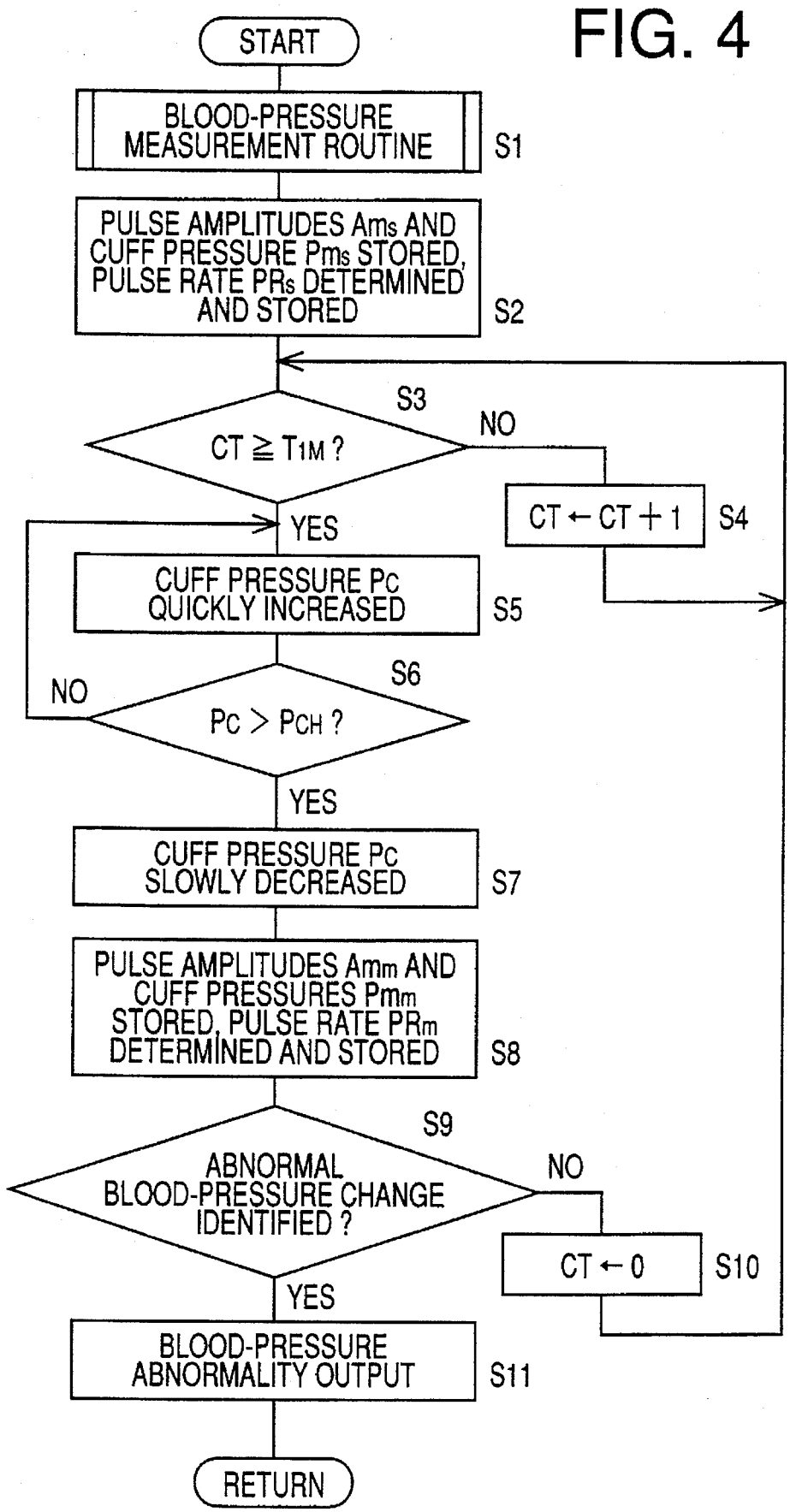
FIG. 4 is a flow chart representing a control program according to which the control device of FIG. 1 functions as illustrated in FIG. 2.
Figure 5:
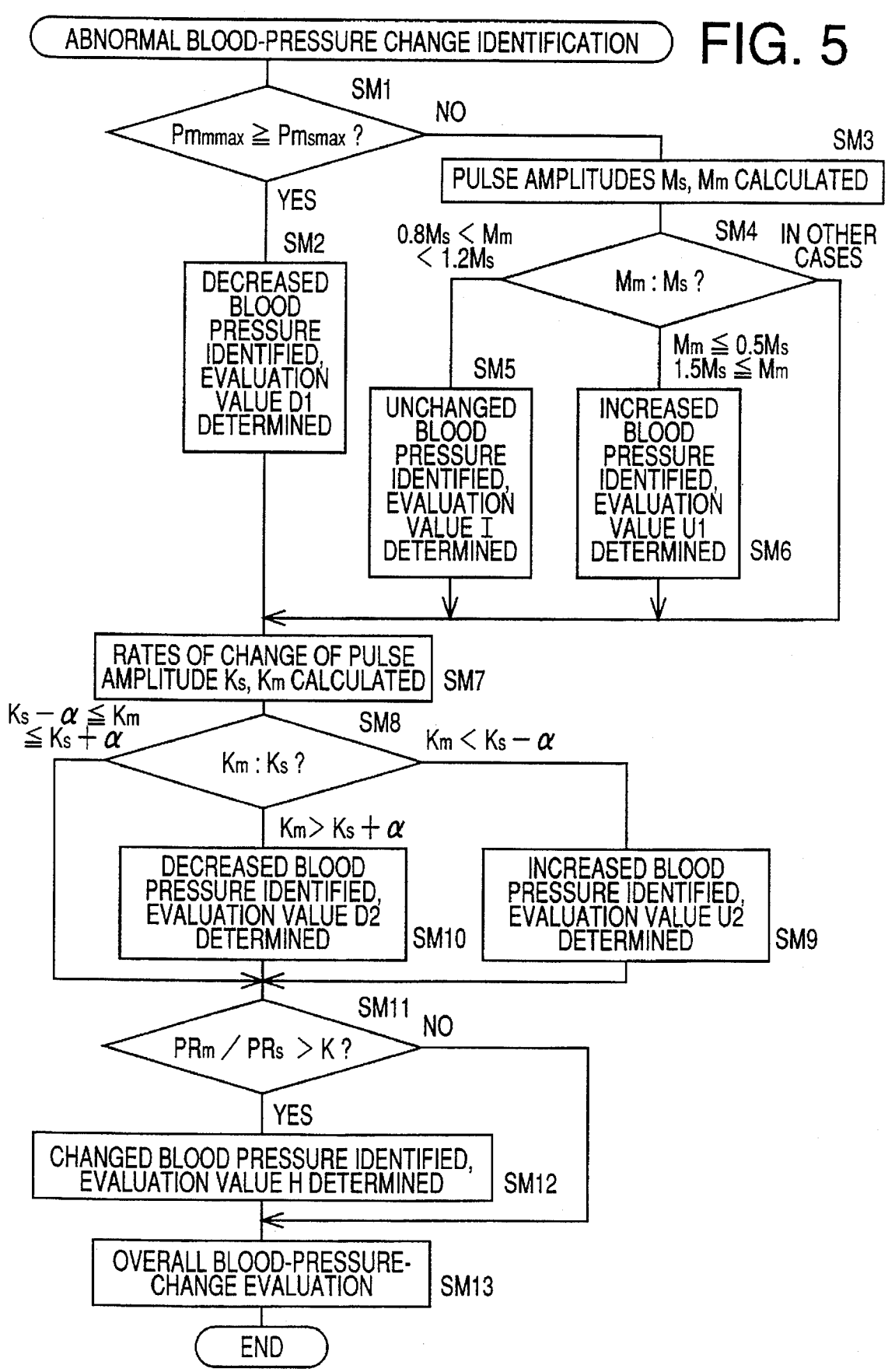
FIG. 5 is a flow chart representing an abnormal blood-pressure change identifying routine carried out at Step S9 of FIG. 4.

At steps not shown in FIG. 4, the CPU 28 of the control device 26 judges whether the start/stop switch 42 has been operated to start the present BP monitor, and judges whether the mode-selection switch 40 has been operated to select the continuous-monitor mode. If positive judgments are made at the two steps, the control of the CPU 28 carries out Step S1, i.e., BP measuring routine that provides part of the BP measuring device 54. At Step S1 corresponding to the initial BP-measuring period shown in FIG. 3, the pressing pressure Pc of the cuff 10 is quickly increased up to a target value, $P_{CM}$, which is pre-determined to be higher than a systolic blood pressure of the subject and subsequently is slowly decreased at 2 to 3 mmHg/sec. A cuff pressure at which pulse amplitudes being detected largely increase during the slow decreasing of the cuff pressure Pc, is determined as a systolic blood pressure $P_{SYS}$ of the subject; a cuff pressure at which the pulse amplitudes largely decrease is determined as a diastolic blood pressure $P_{DIA}$ of the subject; and a cuff pressure at which the greatest pulse amplitude is detected is determined as a mean blood pressure $P_{MEAN}$ of the subject. After the blood pressure measurement is completed, the cuff pressure Pc is quickly decreased.

Figure 6:
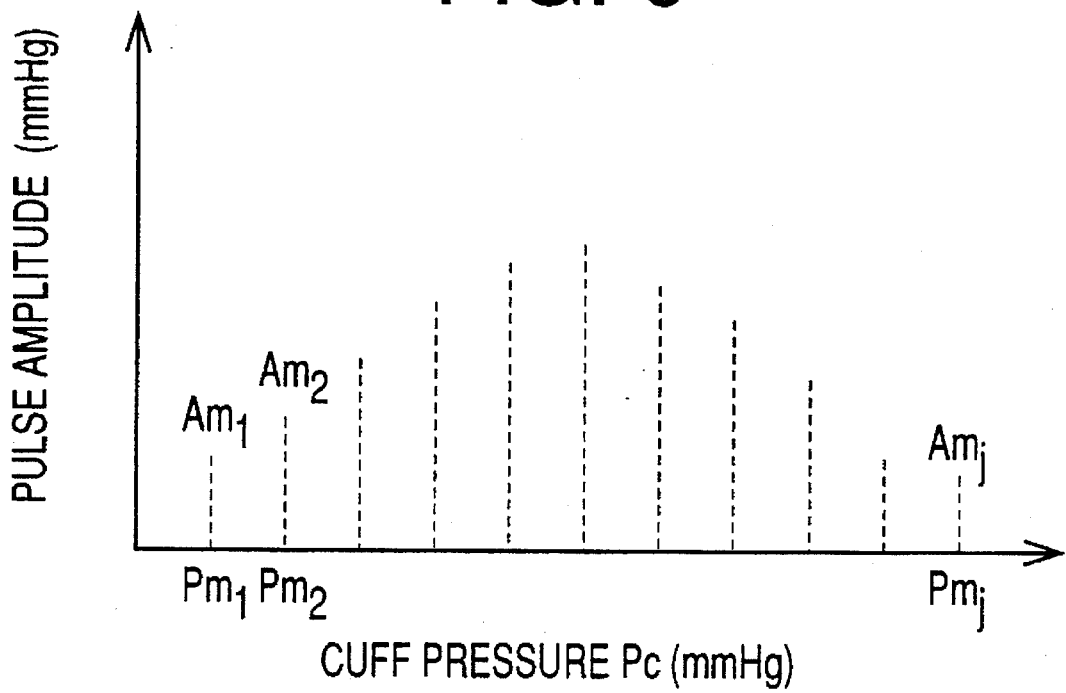
FIG. 6 is a graph showing a series of pulse amplitudes obtained in a BP-measuring period shown in FIG. 3 and stored in a first memory shown in FIG. 2.

Subsequently, at Step S2, the respective amplitudes $Am_s$ (s=1, 2, 3, ..., j) of the heartbeat-synchronous pulses produced as pressure oscillations in the cuff 10 during the slow changing of the cuff pressure Pc in the above BP-measuring period, and the cuff pressures $Pm_s$ (s=1, 2, 3, ..., j) at which the pulse amplitudes $Am_s$ are respectively detected, are stored in an appropriate memory area of the RAM 30. In addition, a pulse rate $PR_s$ of the subject is calculated based on the difference of two times when two successive pulses are respectively detected, and is stored in another appropriate memory area of the RAM 30. FIG. 6 shows an example of a series of pulse amplitudes $Am_s$ stored at Step S2. Thus, the appropriate memory areas of the RAM 30 used at Step S2 provide the first memory 58 and part of the first pulse-rate determining means 66, respectively.

Step S2 is followed by Step S3 to judge. whether a time or contents, CT, measured or counted by a time-signal counter provided in the microcomputer 26, has exceeded a predetermined time interval, $T_{1M}$. The counter CT starts to count the number of time-signals produced after a blood pressure measurement ends at Step S1. The interval $T_{1M}$ is also the interval between each pair of successive BP-monitoring periods following the initial BP-measuring period. At the beginning, negative judgments are made at Step S3, so that the control of the CPU 28 goes to Step S4 to add "one" to the contents CT of the counter and then goes back to Step S3. Thus, Steps S3 and S4 are repeated.

Meanwhile, if a positive judgment is made at Step S3, the control goes to Step S5 to start a first BP-monitoring period shown in FIG. 3, i.e., quickly increase the cuff pressure Pc up to a target value $P_{CH}$ which is pre-determined to be not higher than the measured diastolic blood pressure $P_{DIA}$ of the subject. At Step S6, the CPU 28 judges whether the cuff pressure Pc has been increased to the target value $P_{CH}$. If a positive judgment is made at Step S6, the control goes to Step S7 to slowly decrease the cuff pressure Pc at 2 to 3 mmHg/sec as shown in FIG. 3.

At the following Step S8, the respective amplitudes $Am_m$ (m=1, 2, 3, ..., k) of the heartbeat-synchronous pulses detected during the slow changing of the cuff pressure Pc in the above BP-monitoring period, and the cuff pressures $Pm_m$ (m=1, 2, 3, ..., k) at which the pulse amplitudes $Am_m$ are respectively detected, are stored in an appropriate memory area of the RAM 30. In addition, a pulse rate $PR_m$ of the subject is calculated based on the difference of two times when two successive pulses are respectively detected, and is stored in another appropriate memory area of the RAM 30. Thus, the appropriate memory areas of the RAM 30 used at Step S8 provide the second memory 60 and part of the second pulse-rate determining means 68, respectively.

Step S8 is followed by Step S9, i.e., abnormal BP change identification routine corresponding to part of the BP-change identifying means 70. At Step S9, the CPU 28 judges whether the blood pressure of the subject has been changed abnormally. The abnormal BP-change identification routine of Step S9 will be described in detail by reference to the flow chart of FIG. 5.

Figure 7:
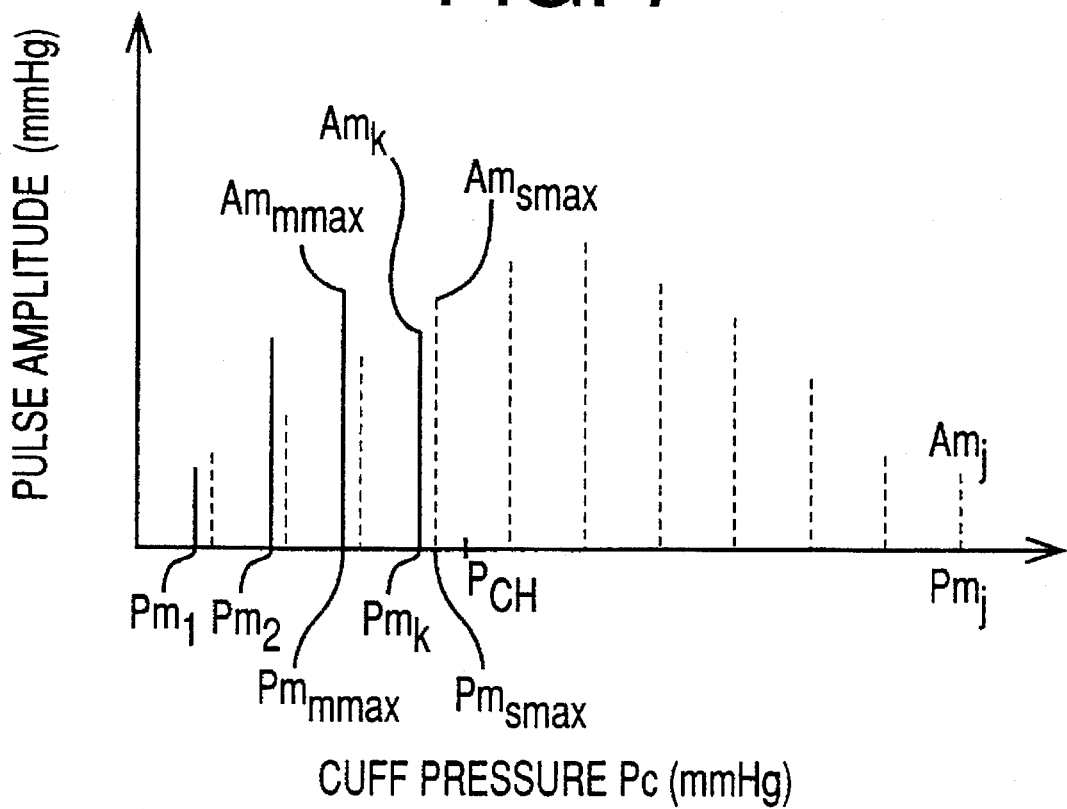
FIG. 7 is a graph showing a series of pulse amplitudes obtained in a BP-monitoring period shown in FIG. 3 and stored in a second memory shown in FIG. 2, in comparison with a series of pulse amplitudes obtained in a BP-measuring period, wherein a cuff pressure, $Pm_{mmax}$, at which the greatest amplitude, $Am_{mmax}$, of the pulse amplitudes, $Am_m$, obtained in the BP-monitoring period in which the cuff pressure Pc is increased to a predetermined value, $P_{CH}$, is lower than a cuff pressure, $Pm_{smax}$, at which the greatest amplitude, $Am_{smax}$, of the pulse amplitudes, $Am_s$, obtained in the BP-measuring period when the cuff pressures Pc are lower than the predetermined pressure $P_{CH}$ is obtained.

First, at Step SM1 corresponding to part of the cuff-pressure comparing means 62, the CPU 28 compares a cuff pressure $Pm_{smax}$ detected at the time of detection of a pulse having the greatest amplitude $Am_{smax}$ out of the pulses which are detected when the cuff pressures Pc are not higher than the predetermined value $P_{CH}$ and stored in the first memory 58, with a cuff pressure $Pm_{mmax}$ detected at the time of detection of a pulse having the greatest amplitude $Am_{mmax}$ out of all the pulses stored in the second memory 60, and judges whether the cuff pressure $Pm_{mmax}$ is lower than the cuff pressure $Pm_{smax}$. If a positive judgment is made at Step SM1, the control goes to Step SM2 to judge that the blood pressure of the subject has decreased, i.e., identify a decrease of the subject's blood pressure. The CPU 28 determines and stores a change evaluation value $D_1$ indicative of a degree of BP decreasing, according to the following function: $D_1 = Pm_{smax} - Pm_{mmax}$, or other appropriate functions of $(Pm_{smax} - Pm_{mmax})$. FIG. 7 shows the case where a positive judgment is obtained at Step SM1.

On the other hand, if a negative judgment is made at Step SM1, the control goes to Step SM3 corresponding to part of specific pulse-amplitude calculating means. At Step SM3, the CPU 28 calculates a specific pulse amplitude $M_s$ of the pulses obtained when the cuff pressures Pc are not higher than the predetermined value $P_{CH}$ and stored in the first memory 58, which amplitude corresponds to a reference cuff pressure value, and a specific pulse amplitude $M_m$ of the pulses stored in the second memory 60, which amplitude corresponds to the reference cuff pressure value. The specific pulse amplitude $M_s$ may be obtained as the value of an envelope or a cumulative curve of the pulse amplitudes $Am_s$ stored in the first memory 58, which value corresponds to the reference cuff pressure value, and the specific pulse amplitude $M_m$ may be obtained as the value of an envelope or a cumulative curve of the pulse amplitudes $Am_m$ stored in the second memory 60, which value corresponds to the reference cuff pressure value.

Figure 8:
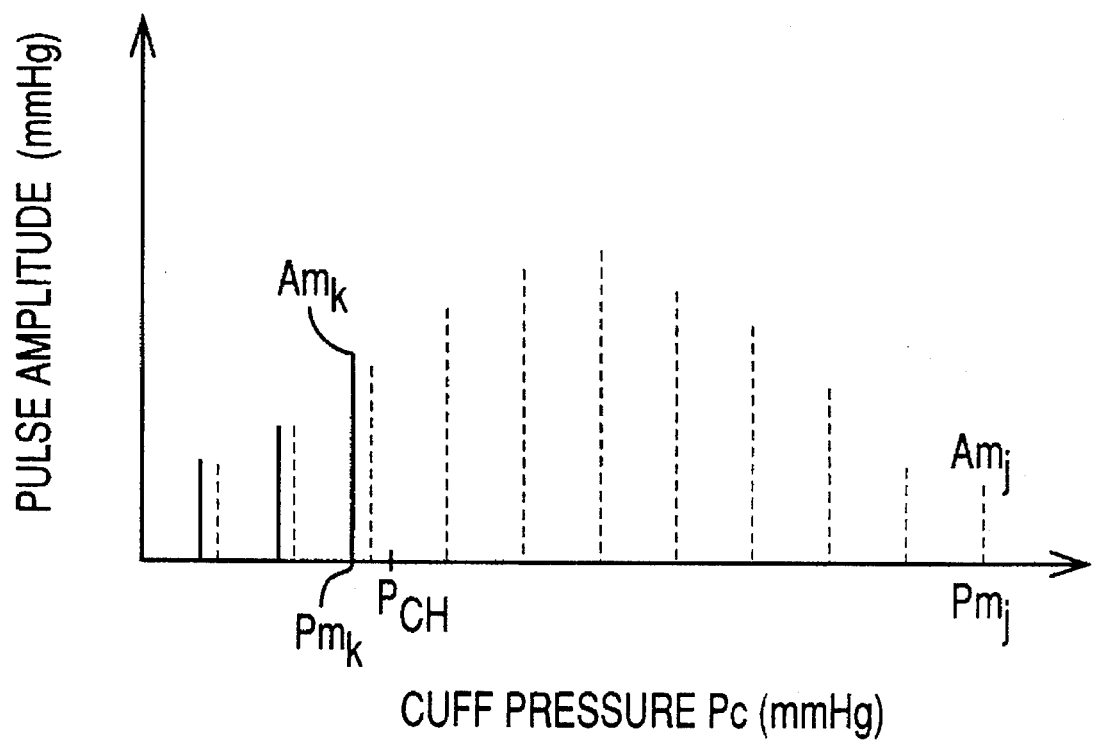
FIG. 8 is a graph showing a series of pulse amplitudes obtained in a BP-monitoring period in comparison with a series of pulse amplitudes obtained in a BP-measuring period, wherein the pulse amplitudes, $Am_m$, obtained in the BP-monitoring period in which the cuff pressure Pc is increased to a predetermined value, $P_{CH}$, are comparable with the pulse amplitudes, $Am_s$, obtained in the BP-measuring period when the cuff pressures Pc are lower than the predetermined pressure $P_{CH}$.

Step SM3 is followed by Step SM4 corresponding to part of pulse-amplitude comparing means. At Step SM4, the CPU 28 compares the specific pulse amplitudes $M_s$, $M_m$. In the case where the pulse amplitude $M_m$ falls within, e.g., the range of ±20% of the pulse amplitude $M_s$, the control of the CPU 28 goes to Step SM5 and judges that the subject's blood pressure has not changed, i.e., identifies the unchanged blood pressure. The CPU 28 determines and stores a non-change evaluation value I indicative of a degree of unchanging of blood pressure, according to the following function: $I = 1/|M_s - M_m|$, or other appropriate functions of $1/|M_s - M_m|$. FIG. 8 shows the case where the pulse amplitude $M_m$ for the BP-monitoring period has not changed from the pulse amplitude $M_s$ for the BP-measuring period.

Figure 9:
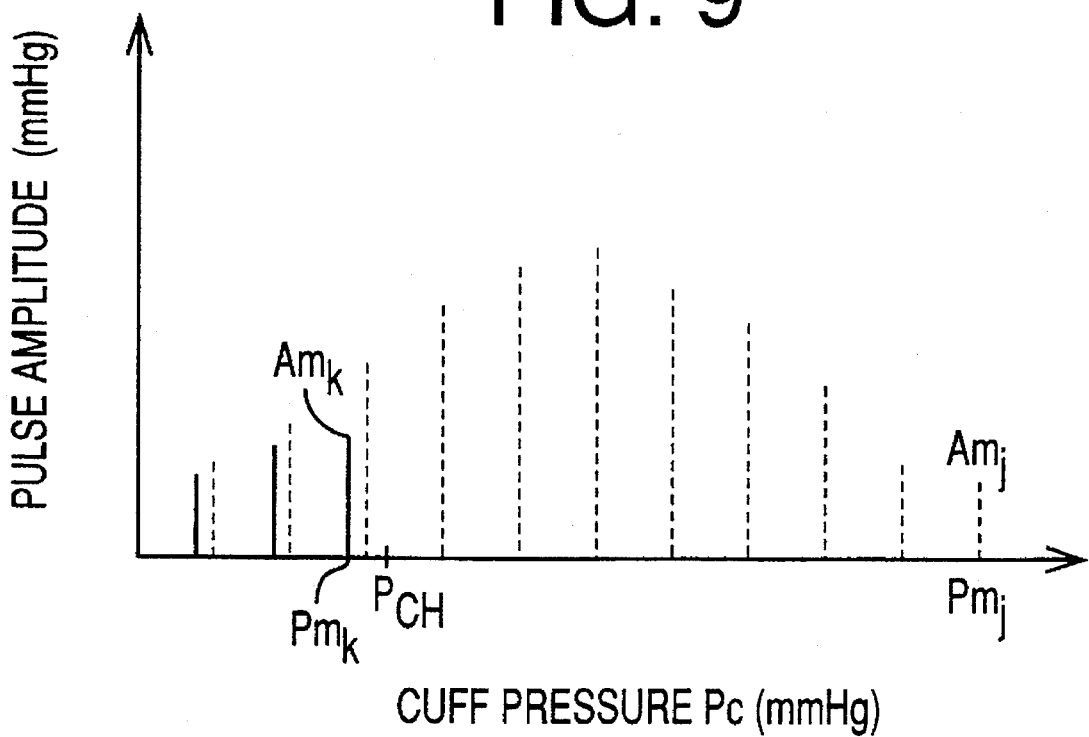
FIG. 9 is a graph showing a series of pulse amplitudes obtained in a BP-monitoring period in comparison with a series of pulse amplitudes obtained in a BP-measuring period, wherein a pulse amplitude, $M_m$, obtained in the BP-monitoring period in which the cuff pressure Pc is increased to a predetermined value, $P_{CH}$, is lower than a pulse amplitude, $M_s$, obtained in the BP-measuring period when the cuff pressures Pc are lower than the predetermined pressure $P_{CH}$, by a predetermined proportion of the pulse amplitude Ms.
Figure 10:
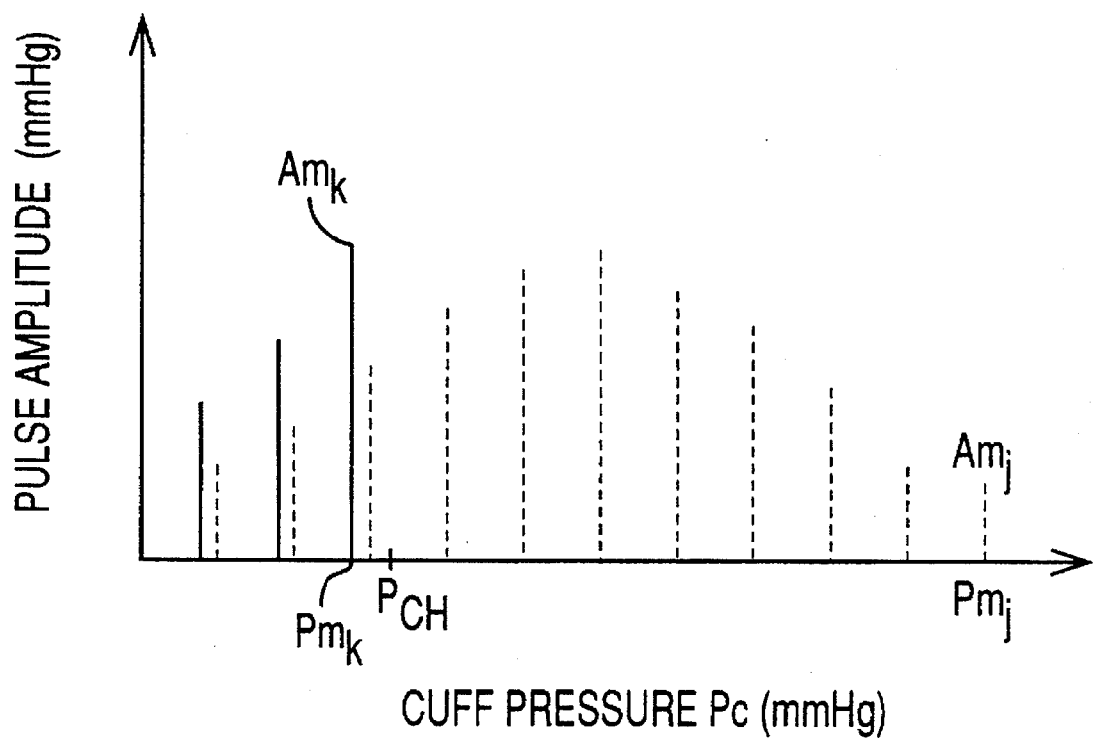
FIG. 10 is a graph showing a series of pulse amplitudes obtained in a BP-monitoring period in comparison with a series of pulse amplitudes obtained in a BP-measuring period, wherein a pulse amplitude, $M_m$, obtained in the BP-monitoring period in which the cuff pressure Pc is increased to a predetermined value, $P_{CH}$, is higher than a pulse amplitude, $M_s$, obtained in the BP-measuring period when the cuff pressures Pc are lower than the predetermined pressure $P_{CH}$.

At Step SM4, in the case where the pulse amplitude $M_m$ does not fall within, e.g., the range of ±50% of the pulse amplitude $M_s$, the control goes to Step SM6 and judges that the subject's blood pressure has increased, i.e., identifies an increase of the blood pressure. The CPU 28 determines and stores a change evaluation value $U_1$ indicative of a degree of BP increasing, according to the following function: $I = |M_s - M_m|$, or other appropriate functions of $|M_s - M_m|$. FIGS. 9 and 10 show the case where the pulse amplitude $M_m$ has decreased from the pulse amplitude $M_s$ and the case where the pulse amplitude $M_m$ has increased from the pulse amplitude $M_s$, respectively.

Figure 11:
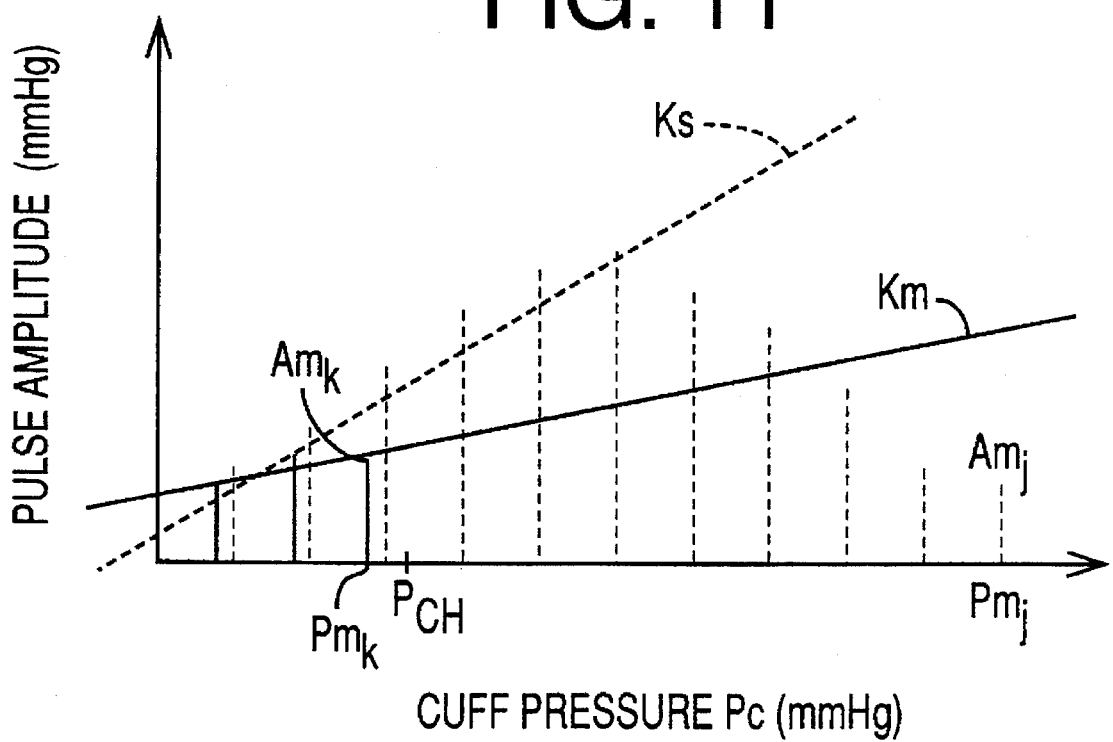
FIG. 11 is a graph showing a series of pulse amplitudes obtained in a BP-monitoring period in comparison with a series of pulse amplitudes Obtained in a BP-measuring period, wherein a rate of change, $K_m$, of the pulse amplitudes, $Am_m$, obtained in the BP-monitoring period in which the cuff pressure Pc is increased to a predetermined value, $P_{CH}$, is smaller than a rate of change, $K_s$, of the pulse amplitudes, $Am_s$, obtained in the BP-measuring period when the cuff pressures Pc are lower than the predetermined pressure $P_{CH}$.
Figure 12:
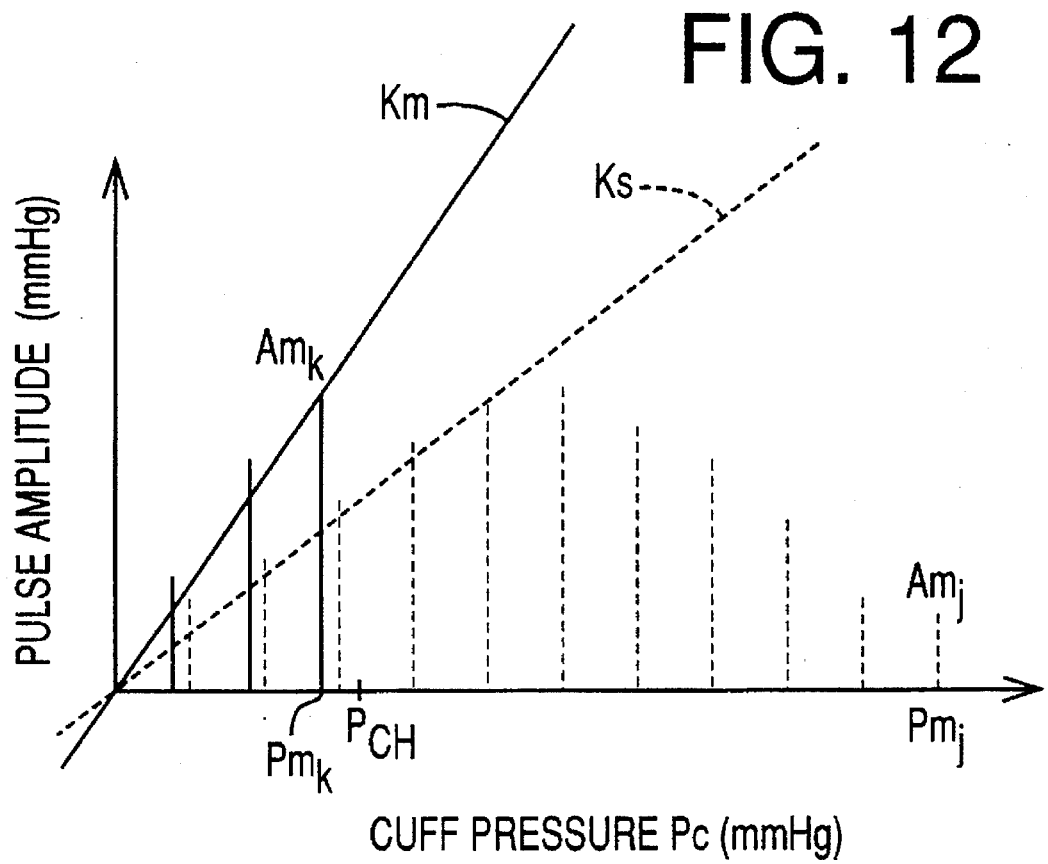
FIG. 12 is a graph showing a series of pulse amplitudes obtained in a BP-monitoring period in comparison with a series of pulse amplitudes obtained in a BP-measuring period, wherein a rate of change, $K_m$, of the pulse amplitudes, $Am_m$, obtained in the BP-monitoring period in which the cuff pressure Pc is increased to a predetermined value, $P_{CH}$, is greater than a rate of change, $K_s$, of the pulse amplitudes, $Am_s$, obtained in the BP-measuring period when the cuff pressures Pc are lower than the predetermined pressure $P_{CH}$.

In the other cases than described above, the control directly goes to Step SM7 corresponding to part of the rate-of-change calculating means 64. At Step SM7, the CPU 28 calculates a rate of change $K_s$ of the respective pulse amplitudes $Am_s$ detected and stored in the first memory 58 when the cuff pressures Pc are not higher than the predetermined value $P_{CH}$, with respect to the corresponding cuff pressures $Pm_s$ stored in the same memory 58, and a rate of change $K_m$ of the respective pulse amplitudes $Am_m$ stored in the second memory 60 with respect to the corresponding cuff pressures $Pm_m$ stored in the same memory 60. The rate of change $K_s$ may be determined as, e.g., the slope of a regression line determined based on data points plotted in a two-dimensional coordinate system having an axis of abscissa indicative of the cuff pressure Pc and an axis of ordinate indicative of the pulse amplitude as shown in FIG. 11 or 12.

Step SM7 is followed by Step SM8 to compare the rates of change $K_s$, $K_m$ with each other. In the case where the rate of change $K_m$ is smaller by more than a predetermined positive value, α, than the rate of change $K_s$, the control goes to Step SM9 and judges that the subject's blood pressure has increased, i.e., identifies a BP increase. The CPU 28 determines and stores a change evaluation value $U_2$ indicative of a degree of BP increasing, according to the following function: $U_2 = K_s - K_m$, or other appropriate functions of $(K_s - K_m)$. FIG. 11 shows the case where the pulse amplitude $K_m$ has decreased from the pulse amplitude $K_s$. On the other hand, in the case where the rate of change $K_m$ is greater by more than the predetermined value α than the rate of change $K_s$, the control goes to Step SM10 and judges that the subject's blood pressure has decreased, i.e., identifies a BP decrease. The CPU 28 determines and stores a change evaluation value $D_2$ indicative of a degree of BP decreasing, according to the following function: $D_2 = K_m - K_s$, or other appropriate functions of $(K_m - K_s)$. FIG. 12 shows the case where the pulse amplitude $K_m$ has increased from the pulse amplitude $K_s$.

Figure 13:
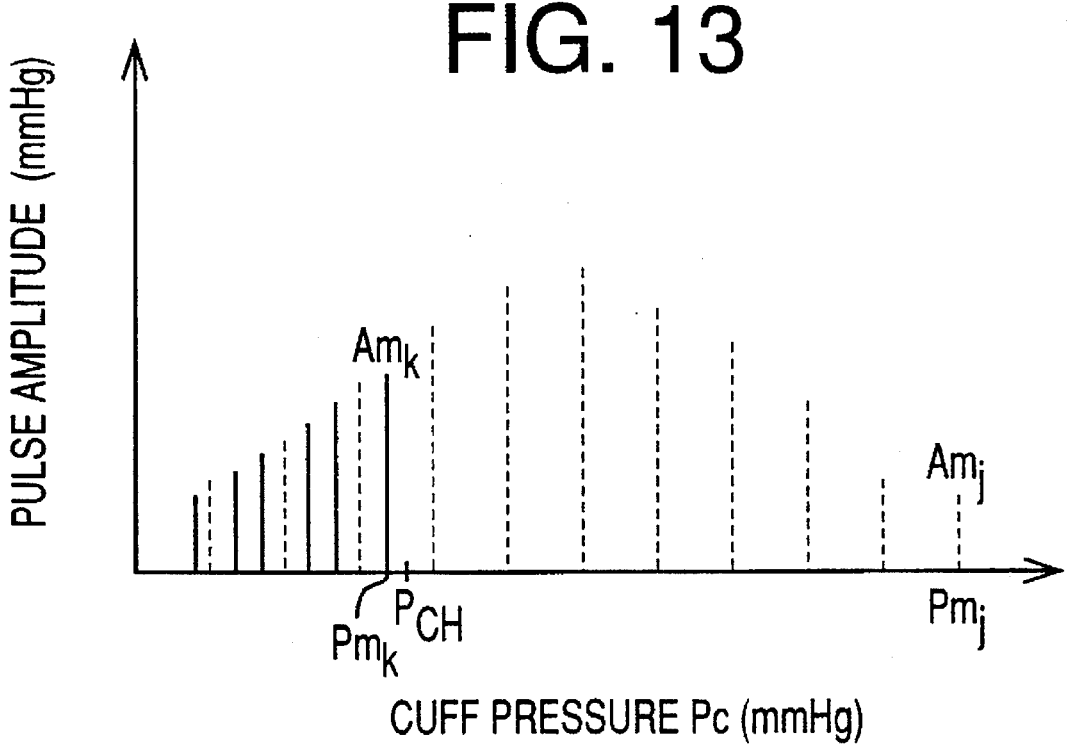
FIG. 13 is a graph showing a series of pulse amplitudes obtained in a BP-monitoring period in comparison with a series of pulse amplitudes obtained in a BP-measuring period, wherein a pulse rate, $PR_m$, determined from the pulse amplitudes, $Am_m$, obtained in the BP-monitoring period in which the cuff pressure Pc is increased to a predetermined value, $P_{CH}$, is higher than a pulse rate, $PR_s$, determined from the pulse amplitudes, $Am_s$, obtained in the BP-measuring period when the cuff pressures Pc are lower than the predetermined pressure $P_{CH}$.
Figure 14:
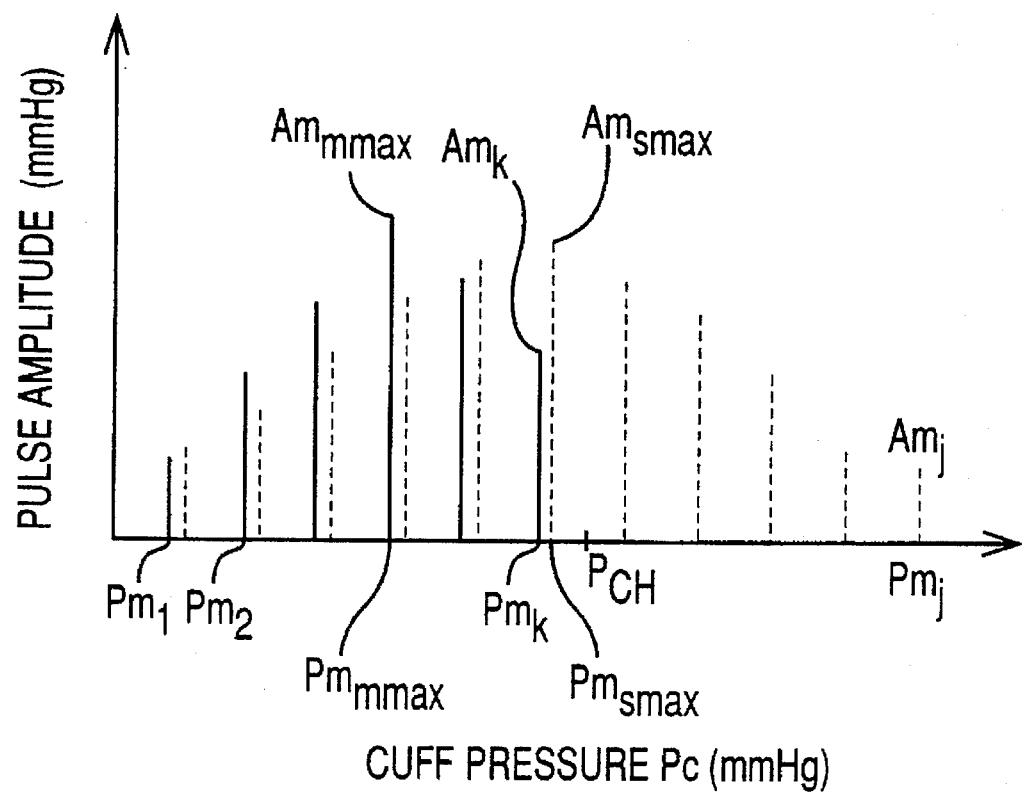
FIG. 14 is a graph, corresponding to the graph of FIG. 7, wherein in a BP-monitoring period the cuff pressure Pc is increased to a predetermined value $P_{CH}$ slightly higher than a mean blood pressure, $P_{MEAN}$, of a living subject.
Figure 15:
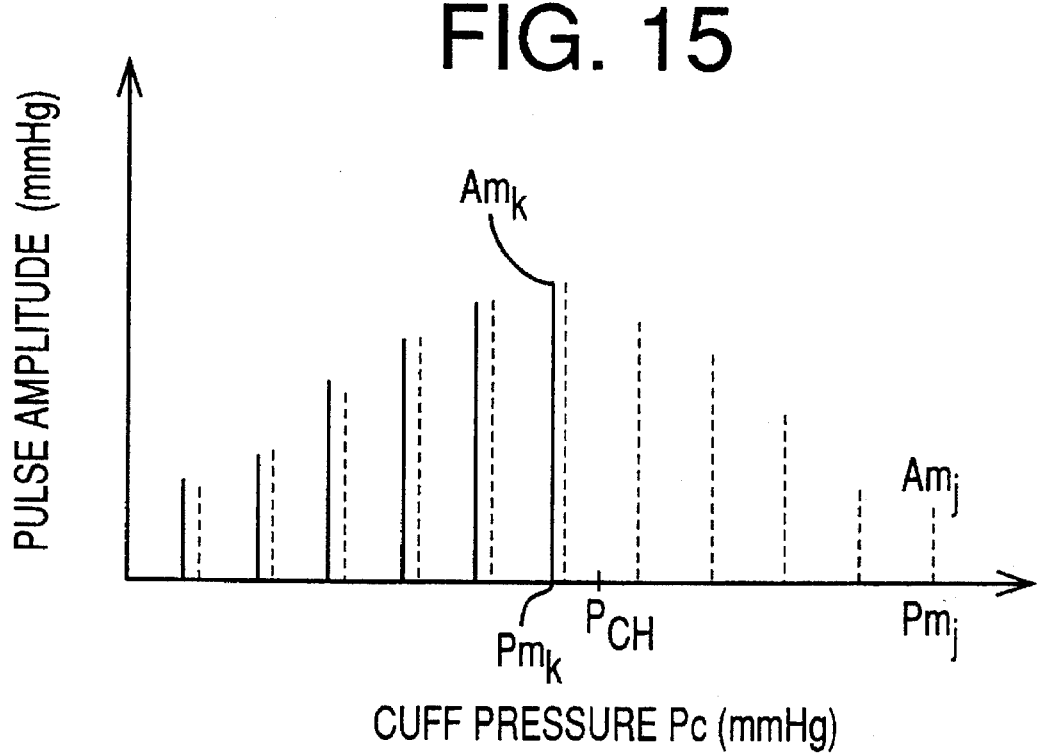
FIG. 15 is a graph, corresponding to the graph of FIG. 8, wherein in a BP-monitoring period the cuff pressure Pc is increased to a predetermined value $P_{CH}$ slightly higher than a mean blood pressure $P_{MEAN}$ of a living subject.
Figure 16:
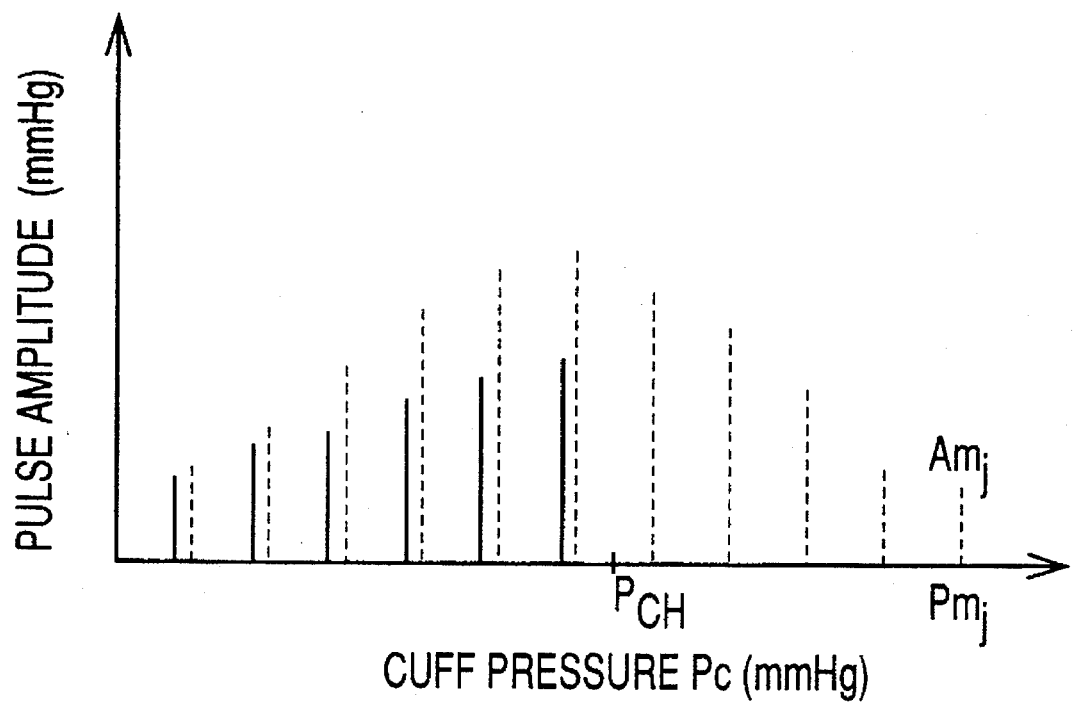
FIG. 16 is a graph, corresponding to the graph of FIG. 9, wherein in a BP-monitoring period the cuff pressure Pc is increased to a predetermined value $P_{CH}$ slightly higher than a mean blood pressure $P_{MEAN}$ of a living subject.
Figure 17:
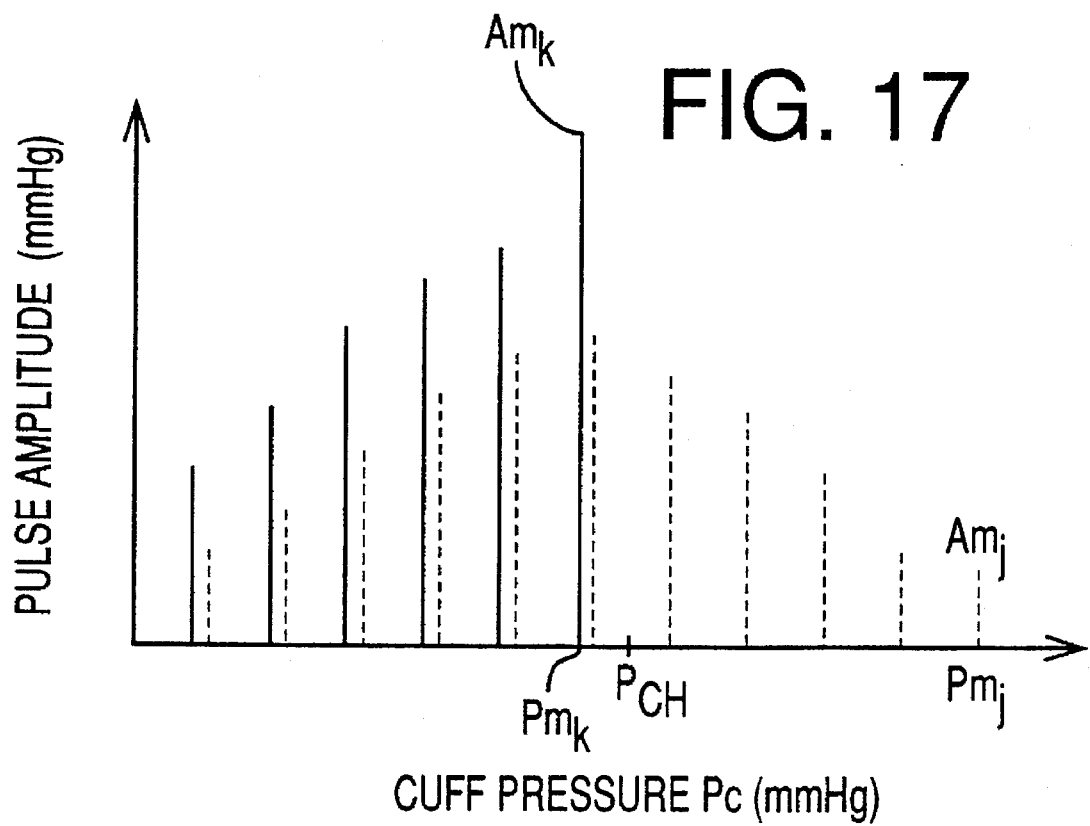
FIG. 17 is a graph, corresponding to the graph of FIG. 10, wherein a BP-monitoring period the cuff pressure Pc is increased to a predetermined value $P_{CH}$ slightly higher than a mean blood pressure $P_{MEAN}$ of a living subject.
Figure 18:
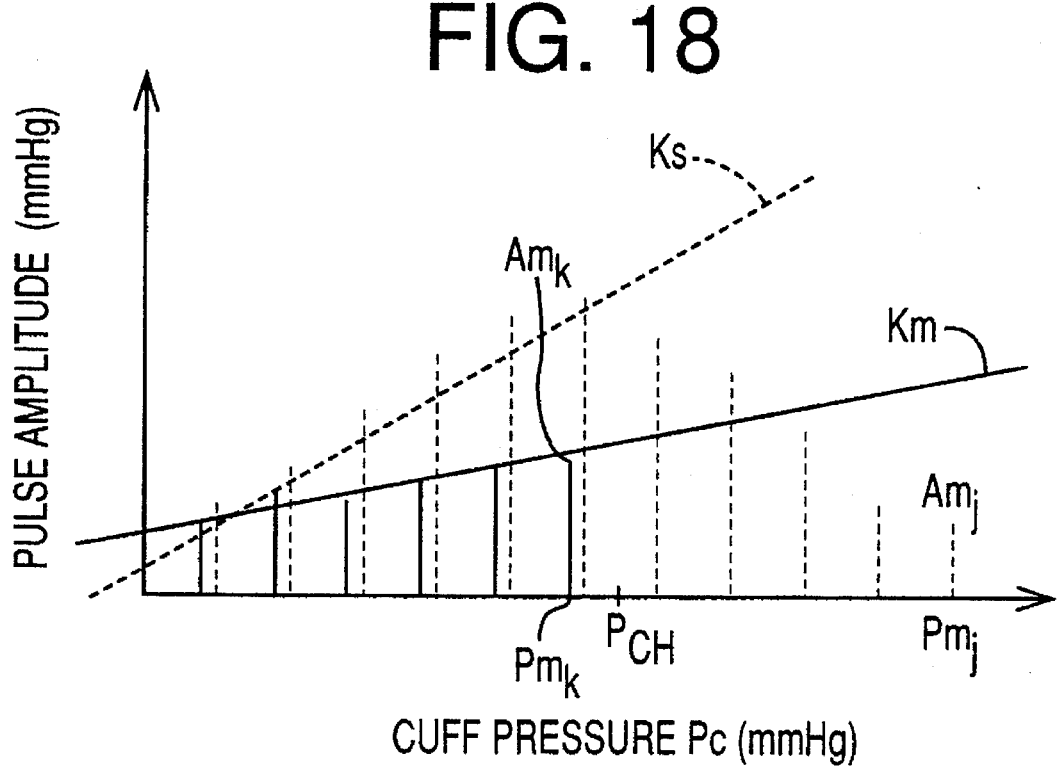
FIG. 18 is a graph, corresponding to the graph of FIG. 11, wherein in a BP-monitoring period the cuff pressure Pc is increased to a predetermined value $P_{CH}$ slightly higher than a mean blood pressure $P_{MEAN}$ of a living subject.
Figure 19:
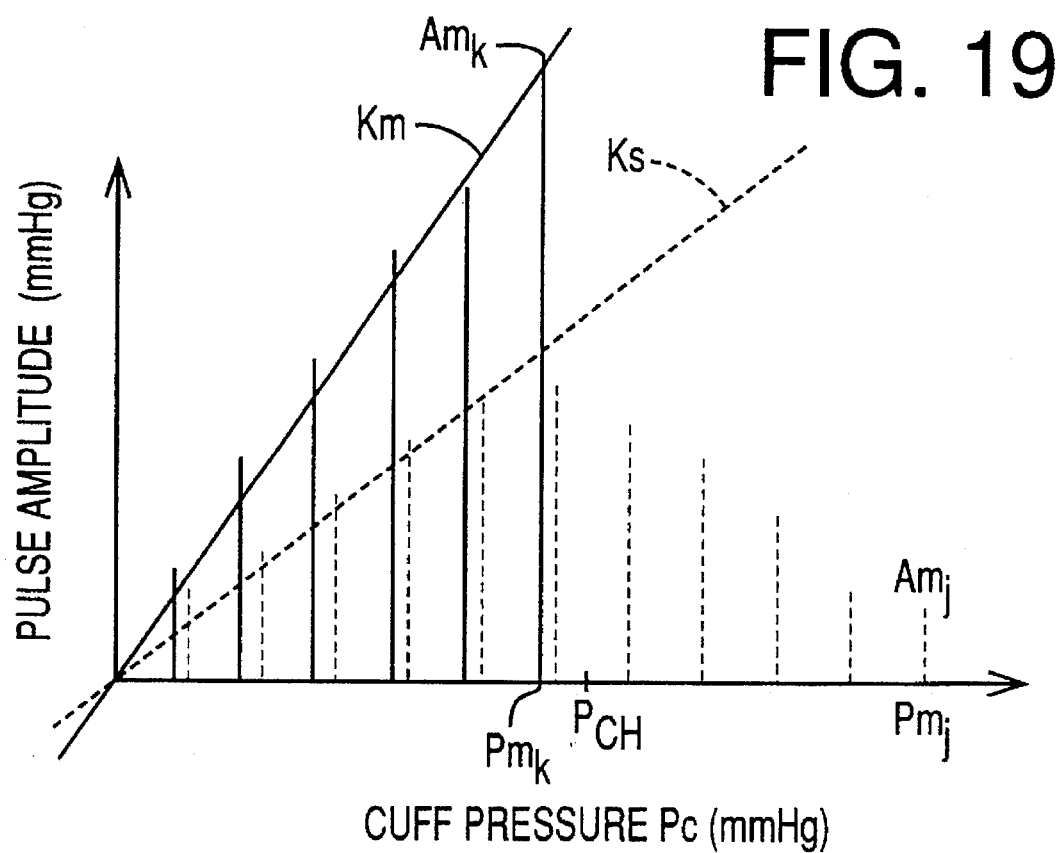
FIG. 19 is a graph, corresponding to the graph of FIG. 12, wherein in a BP-monitoring period the cuff pressure Pc is increased to a predetermined value $P_{CH}$ slightly higher than a mean blood pressure $P_{MEAN}$ of a living subject.
Figure 20:
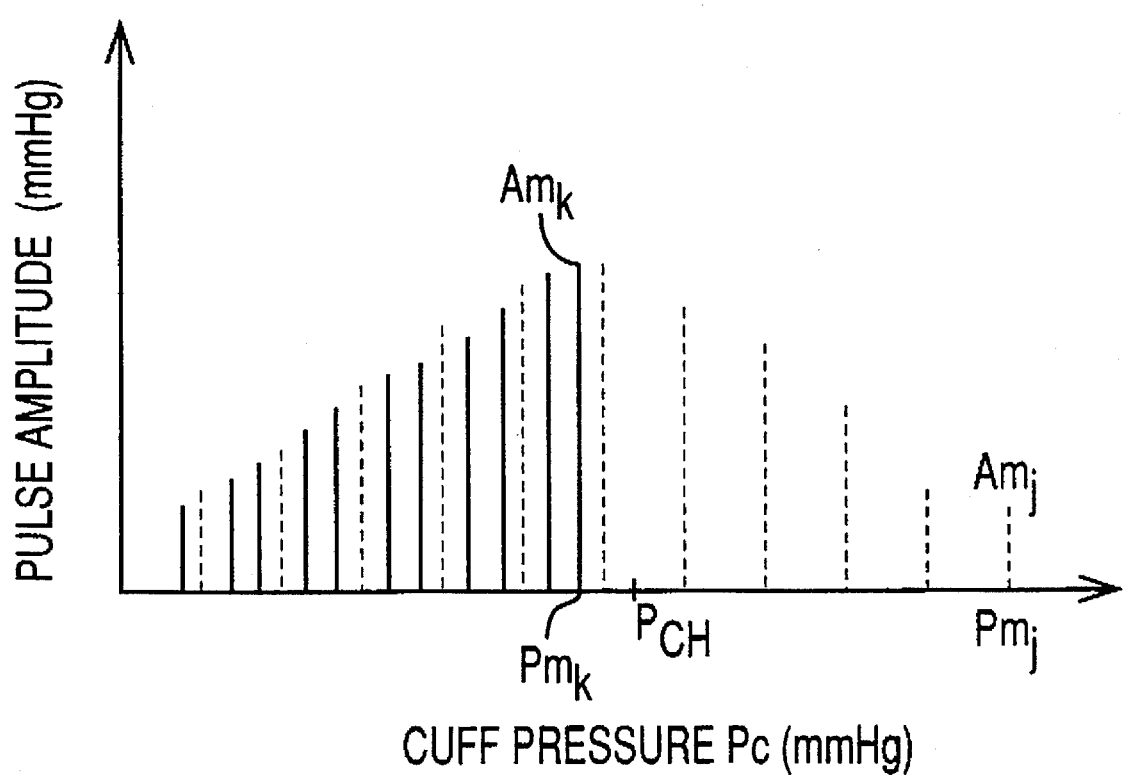
FIG. 20 is a graph, corresponding to the graph of FIG. 13, wherein in a BP-monitoring period the cuff pressure Pc is increased to a predetermined value $P_{CH}$ slightly higher than a mean blood pressure $P_{MEAN}$ of a living subject.

In the other cases than described above, the control directly goes to Step SM11 to compare the pulse rate $PR_s$ of the subject determined based on the pulses obtained in a BP-measuring period, with the pulse rate $PR_m$ of the subject determined based on the pulses obtained in a BP-monitoring period after the BP-measuring period, and judge whether a ratio of the pulse rate $PR_m$ to the pulse rate $PR_s$, $PR_m/PR_s$, is greater than a predetermined value, K, greater than one. If a negative judgment is made at Step SM11, the control of the CPU 28 skips Step SM12 and directly goes to Step SM13. On the other hand, if a positive judgment is made, the control goes to Step SM12 and judges that the subject's blood pressure has changed, i.e., identifies a BP change. The CPU 28 determines and stores a change evaluation value H indicative of a degree of BP changing, according to the following function: $H = PR_m/PR_s$, or other appropriate functions of $PR_m/PR_s$. FIG. 13 shows the case where the pulse rate $PR_m$ has changed from the pulse rate $PR_s$.

At Step SM13, the CPU 28 makes an overall evaluation on the change of the subject's blood pressure, based on the change evaluation values $D_1$, $D_2$, non-change evaluation value I, change evaluation values $U_1$, $U_2$, and change evaluation value H, i.e., obtains an overall evaluation value S according to the previously-described expression (1). If the overall evaluation value S does not fall within a reference range, the CPU 28 judges that the subject's blood pressure has abnormally increased or decreased.

If at Step SM13 the CPU 28 does not identify an abnormal BP change, a negative judgment is made at Step S9 of FIG. 4, so that the control goes to Step S10 to clear or reset the contents CT of the timer and then repeats Step S3 and the following steps. On the other hand, if a positive judgment is made at Step S9, the control goes to Step S11 to operate the output device 38 to inform the user of the identification of the abnormal BP change, and operates the BP re-measuring device 72 to immediately start a BP measuring period and carry out a BP measurement on the subject like at Step S1. Thus, the output device 38 displays and/or records the subject's BP values measured immediately after the identification of the abnormal BP change. Thus, Step S11 corresponds to part of the BP re-measuring device 72.

As is apparent from the foregoing description, in the present embodiment, the pulse amplitudes $Am_s$ (s=1 to j) are detected as the pressure oscillations produced in the cuff 10 during the slowing decreasing of the cuff pressure Pc, in a BP measurement carried out at Step S1 corresponding to part of the BP measuring device 54, and the pulse amplitudes $Am_s$ and the cuff pressures $pm_s$ (s=1 to j) detected at the respective times of detection of the pulse amplitudes $Am_s$, are stored in the first memory 58. In addition, the pulse amplitudes $Am_m$ (m=1 to k) are detected during the slowing decreasing of the cuff pressure Pc from the predetermined value $P_{CH}$, in each of BP monitoring periods following a BP measurement of the BP-measuring device 54, and the pulse amplitudes $Am_m$ and the cuff pressures $Pm_m$ (m=1 to k) detected at the respective times of detection of the pulse amplitudes $Am_m$ are stored in the second memory 60. At Step S9 corresponding to part of the BP-change identifying means 70, a change of the blood pressure of the subject is identified based on the pulse amplitudes $Am_s$ and cuff pressures $Pm_s$ stored in the first memory 58 and the pulse amplitudes $Am_m$ and cuff pressures $Pm_m$ stored in the second memory 60.

The present BP monitor can monitor the blood pressure of the subject with high accuracy, because the apparatus identifies a change of the subject's blood pressure based on both the pulse amplitudes $Am_s$ and cuff pressures $pm_s$ obtained in a BP-measuring period and the pulse amplitudes $Am_m$ and cuff pressures $pm_m$ obtained in a BP-monitoring period. In addition, since the BP monitor monitors the subject's blood pressure by iteratively changing the cuff pressure Pc within a low pressure range between the atmospheric pressure and the pre-determined pressure value $P_{CH}$ lower than the subject's diastolic blood pressure $P_{DIA}$, the apparatus does not cause the subject to feel serious discomfort.

In the present embodiment, the BP monitor makes an overall evaluation on the change of the subject's blood pressure, based on the change evaluation values $D_1$, $D_2$, non-change evaluation value I, change evaluation values $U_1$, $U_2$, and change evaluation value H, according to the previously-described expression (1). Thus, the BP monitor can monitor the subject's blood pressure with high reliability.

If an abnormal BP change is identified by the BP-change identifying means 70, the BP re-measuring device 72 immediately carries out a BP measurement using the cuff 10, and outputs the BP values obtained at the time of identification of the abnormal BP change. Thus, a medical worker such as a doctor or a nurse can quickly give appropriate treatments on the subject.

Figure 21:
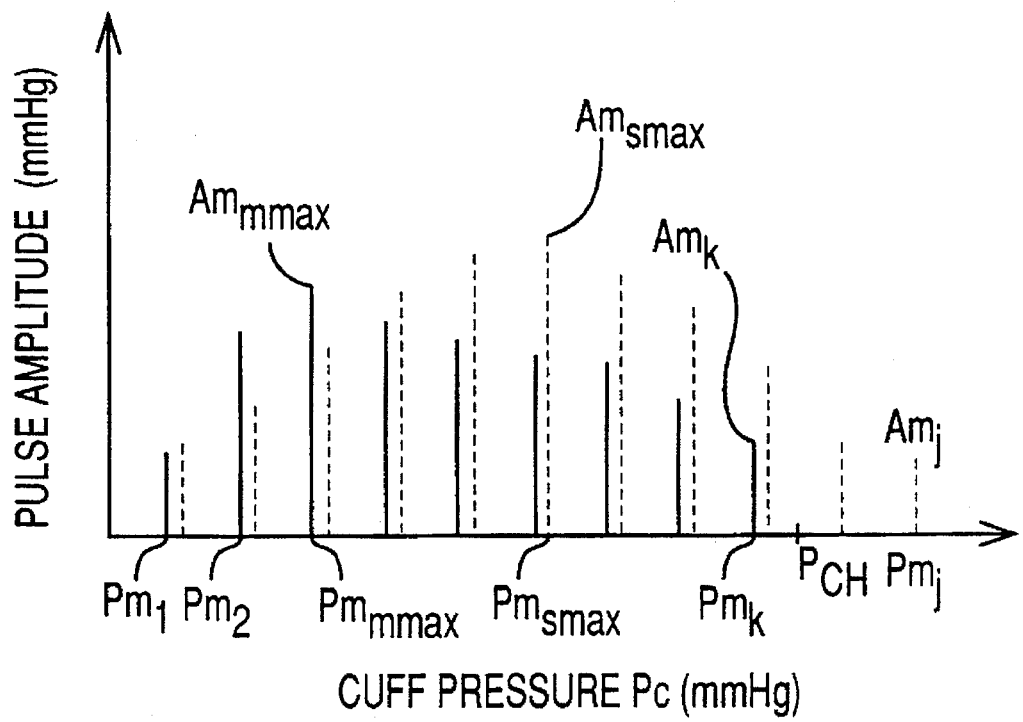
FIG. 21 is a graph, corresponding to the graph of FIG. 7, wherein in a BP-monitoring period the cuff pressure Pc is increased to a predetermined value $P_{CH}$ lower than a systolic blood pressure, $P_{SYS}$, of a living subject by a predetermined value.
Figure 22:
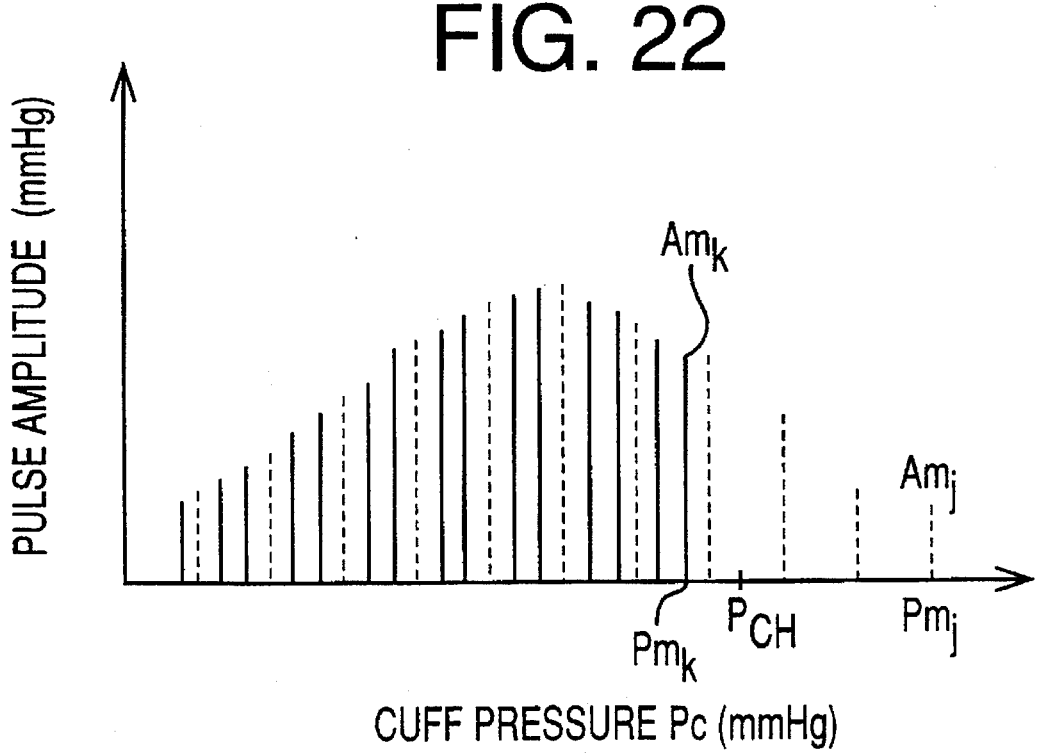
FIG. 22 is a graph, corresponding to the graph of FIG. 13, wherein in a BP-monitoring period the cuff pressure Pc is increased to a predetermined value $P_{CH}$ lower than a systolic blood pressure $P_{SYS}$ of a living subject by a predetermined value.

In the present embodiment, the cuff-pressure control device 56 increases, in each BP-monitoring period, the cuff pressure Pc up to a target value $P_{CH}$ which is predetermined to be not higher than the subject's diastolic blood pressure $P_{DIA}$. However, the cuff-pressure control device 56 may be modified to increase, in each BP-monitoring period, the cuff pressure Pc up to a different target value $P_{CH}$ which is predetermined to be slightly higher than the subject's mean blood pressure $P_{MEAN}$. FIGS. 14 to 20 correspond to FIGS. 7 to 13, respectively, and show the cases where the cuff pressure Pc is increased to a predetermined target value $P_{CH}$ slightly higher than the mean blood pressure $P_{MEAN}$. Moreover, the cuff-pressure control device 56 may be modified to increase, in each BP-monitoring period, the cuff pressure Pc up to a different target value $P_{CH}$ which is predetermined to be higher than the mean blood pressure $P_{MEAN}$ and lower by a predetermined value than the systolic blood pressure $P_{SYS}$. FIGS. 21 and 22 correspond to FIGS. 7 and 13, respectively, and show the cases where the cuff pressure Pc is increased to a predetermined target value $P_{CH}$ higher than the mean blood pressure $P_{MEAN}$ and lower than the systolic blood pressure $P_{SYS}$.

Next, there will be described a second embodiment of the present invention. The second embodiment also relates to a BP monitor and has the same hardware construction as that of the first embodiment shown in FIG. 1. However, the second BP monitor is operated according to the control program represented by the flow charts of FIGS. 27 and 28 in place of the program represented by the flow charts of FIGS. 4 and 5 for the first embodiment.

Figure 23:
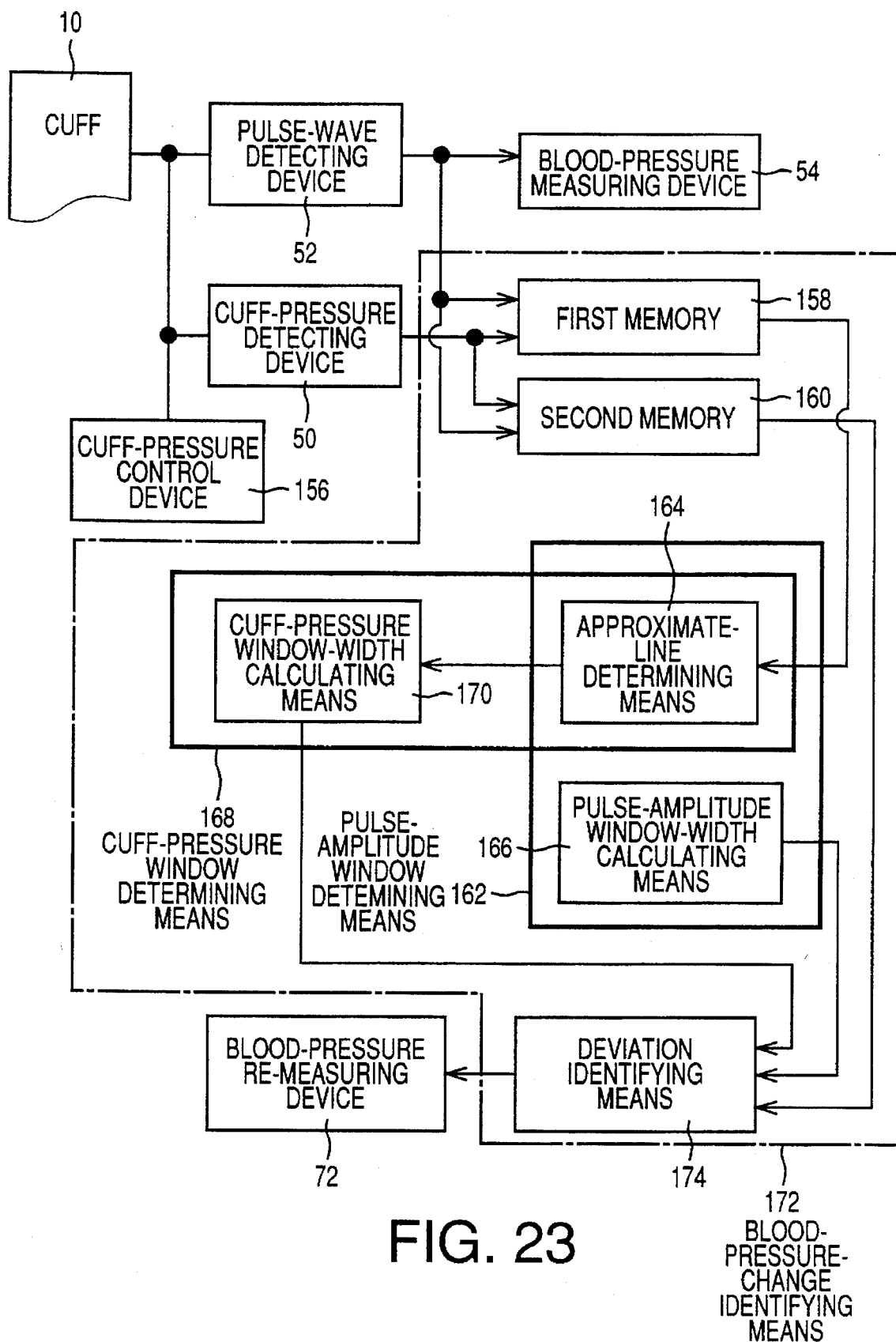
FIG. 23 is a diagrammatic view corresponding to FIG. 2, for illustrating various functions of a control device of another blood-pressure monitor apparatus as a second embodiment of the invention.

FIG. 23 shows various functions of a control device 26 of the second BP monitor. The second BP monitor includes an inflatable cuff 10, a cuff-pressure detecting device 50, a pulse-wave detecting device 52, an oscillometric BP measuring device 54, and a BP re-measuring device 72 all of which are the same as the counterparts of the first BP monitor shown in FIG. 2.

The second BP monitor includes a cuff-pressure control device 156 which quickly increases, in a BP-measuring period of the BP measuring device 54 shown in FIG. 29, a pressing pressure Pc of the cuff 10 to a target pressure $P_{CM}$ which is pre-determined to be higher than a systolic blood pressure of the subject, and subsequently slowly decreases the cuff pressure Pc at 2 to 3 mmHg/sec. In a non-measurement period in which the BP measuring device 54 does not work, the cuff-pressure control device 156 iteratively increases and decreases the cuff pressure Pc to and from a target pressure value, $P_{CH}$, which is predetermined to be not higher than a mean blood pressure $P_{MEAN}$ of the subject, while inserting a predetermined rest period between successive two BP-monitoring periods. During the slow decreasing of the cuff pressure Pc in each BP-monitoring period, the second BP monitor collects pulse amplitudes and cuff pressures.

Figure 24:
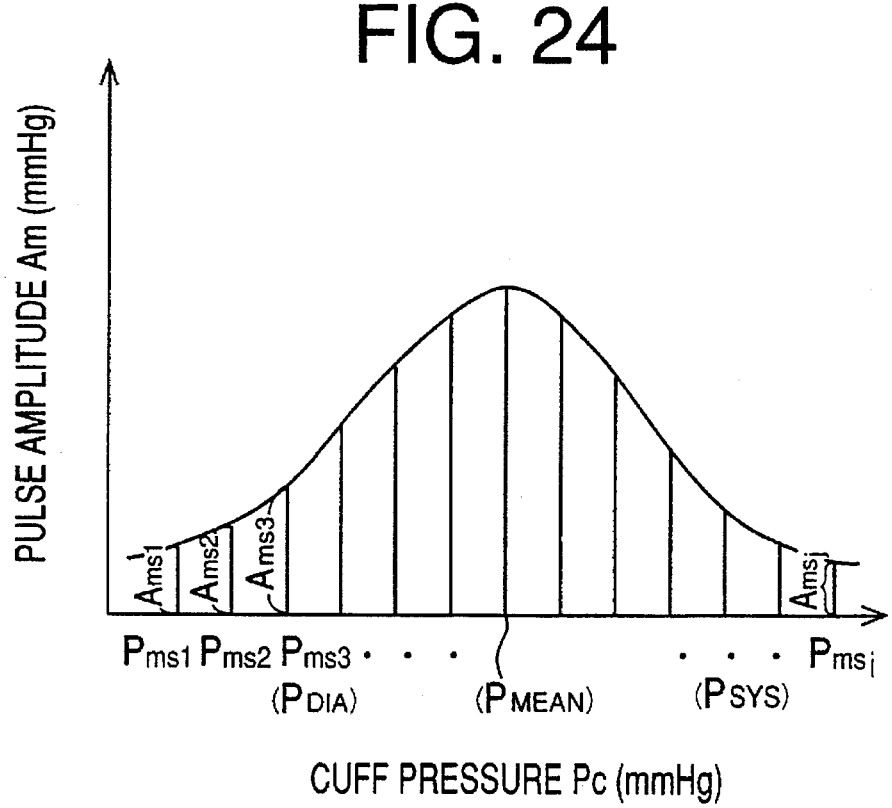
FIG. 24 is a graph showing a series of pulse amplitudes, $Ams_n$, obtained in a BP-measuring period shown in FIG. 29 and stored in a first memory shown in FIG. 23, in relation with cuff pressures, $Pms_n$, when the pulse amplitudes $Ams_n$ are obtained.
Figure 25:
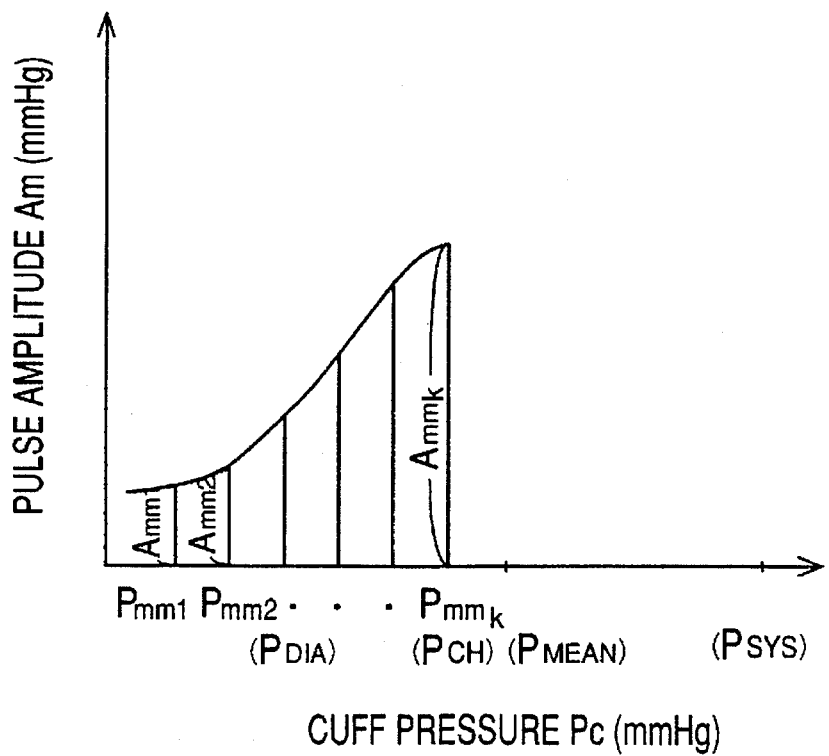
FIG. 25 is a graph showing a series of pulse amplitudes, $Amm_m$, obtained in a BP-monitoring period shown in FIG. 29 and stored in a second memory shown in FIG. 23, in relation with cuff pressures, $Pmm_m$, when the pulse amplitudes $Amm_m$ are obtained.

A first memory 158 stores the respective amplitudes of heartbeat-synchronous pulses, $Ams_n$ (n=1, 2, 3, . . . , j), produced as pressure oscillations in the cuff 10 while the cuff pressure Pc is slowly changed by the BP measuring device 54 in a BP-measuring period. The first memory 158 also stores the cuff pressures, $Pms_n$ (n=1, 2, 3, . . . , j), detected by the cuff-pressure detecting device 50 when the corresponding pulse amplitudes $Ams_n$ are detected by the pulse-wave detecting device 52. FIG. 24 shows a series of pulse amplitudes $Ams_n$ which are obtained as the cuff pressures $pms_n$ are changed. A second memory 160 stores the respective amplitudes of heartbeat-synchronous pulses, $Amm_m$ (m=1, 2, 3, . . . , k), detected by the pulse-wave detecting device 52 while the cuff pressure Pc is slowly changed by the cuff-pressure control device 156 in each BP-monitoring period subsequent to a BP-measuring period, and also stores the cuff pressures, $Pmm_m$ (m=1, 2, 3, . . . , k), detected by the cuff-pressure detecting device 50 when the corresponding pulse amplitudes $Amm_m$ are detected. FIG. 25 shows a series of pulse amplitudes $Amm_m$ which are obtained as the cuff pressures $Pmm_m$ are changed. The first memory 158 stores the pulse amplitudes $Ams_n$ in relation with the corresponding cuff pressures $Pms_n$, and the second memory 160 stores the pulse amplitudes $Amm_m$ in relation with the corresponding cuff pressures $Pmm_m$. Thus, it can be said that the first memory 158 stores a first relationship between the cuff pressures $pms_n$ and the pulse amplitudes $Ams_n$ and that the second memory 160 stores a second relationship between the cuff pressures $Pmm_m$ and the pulse amplitudes $Amm_m$.

Figure 26:
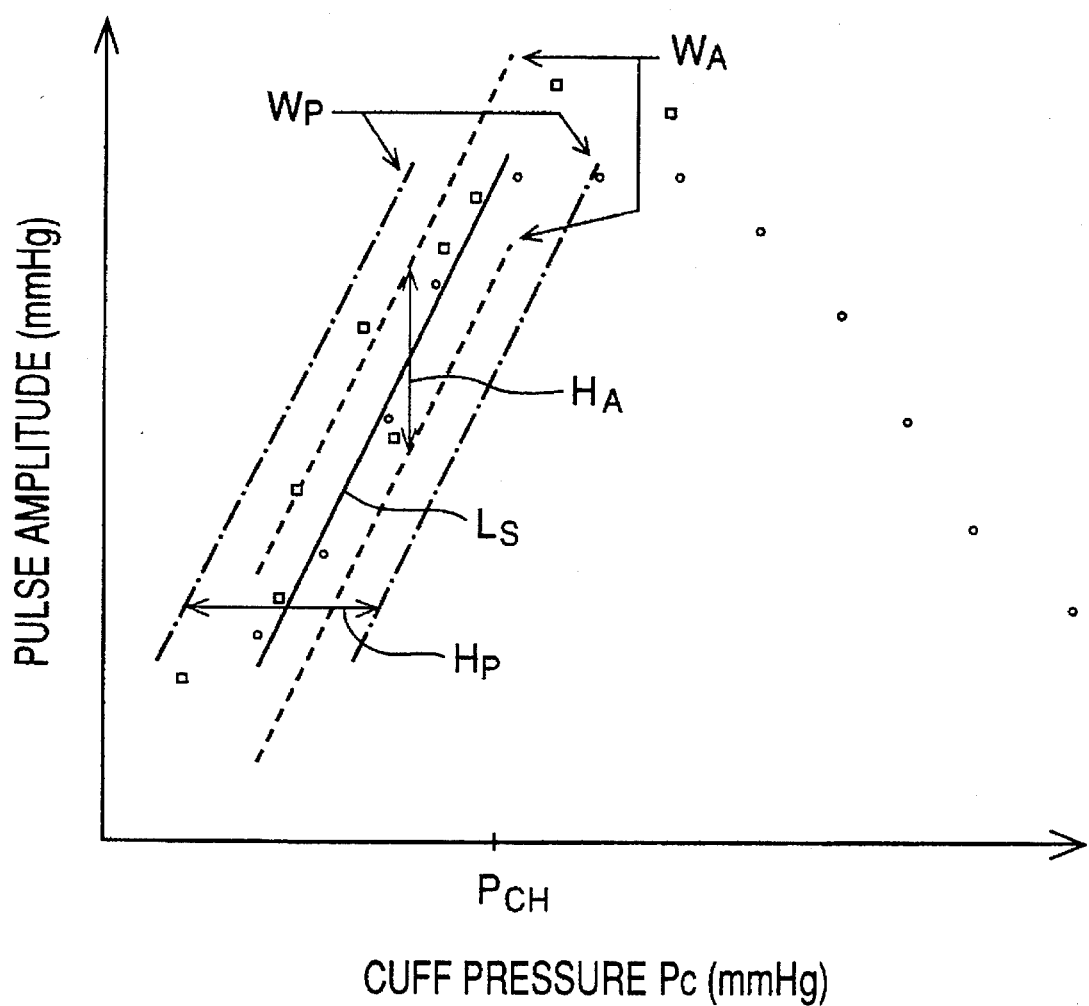
FIG. 26 is a graph for illustrating an approximate line, $L_s$, representing a relationship between the pulse amplitudes and cuff pressures collected in a BP-measuring period; a pulse-amplitude window, $W_A$; and a cuff-pressure window, $W_P$ all of which are determined by the apparatus of FIG. 23.

A pulse-amplitude window determining means 162 determines a Pulse-amplitude window, $W_A$, based on the first relationship between the cuff pressures $Pms_n$ and pulse amplitudes $Ams_n$ stored in the first memory 158. The pulse-amplitude window determining means 162 includes an approximate-line determining means 164 for determining an approximate line, $L_S$, which approximates a portion of the first relationship stored in the first memory 158 which portion falls within a predetermined cuff-pressure range not higher than the subject's mean blood pressure $P_{MEAN}$ (e.g., range between the subject's diastolic blood pressure $P_{DIA}$ and the target pressure value $P_{CH}$), that is, approximates an envelope of the data points which represent the cuff pressures $Pms_n$ falling within the above cuff-pressure range and the corresponding pulse amplitudes $Ams_n$. The approximate-line determining means 164 determines, as the approximate line $L_S$, a least-square approximate line or a regression line based on the above data points. The approximate line $L_S$ is employed as a center line of the pulse-amplitude window $W_A$. The pulse-amplitude window determining means 162 further includes a pulse-amplitude window-width calculating means 166 for calculating a width, $H_A$, of the pulse-amplitude window $W_A$ along the axis of ordinate indicative of the pulse amplitude. The window $W_A$ has respective halves of the width $H_A$ on both sides of the approximate line $L_S$ as the center line thereof, as shown in FIG. 26.

A cuff-pressure window determining means 168 determines a cuff-pressure window, $W_P$, based on the first relationship between the cuff pressures $Pms_n$ and pulse amplitudes $Ams_n$ stored in the first memory 158. The cuff-pressure window determining means 168 includes the above-described approximate-line determining means 164 for determining the approximate line $L_S$, which is employed as a center line of the cuff-pressure window $W_P$. The cuff-pressure window determining means 168 further includes a cuff-pressure window-width calculating means 170 for calculating a width, Hp, of the cuff-pressure window $W_P$ along the axis of abscissa indicative of the cuff pressure Pc. The window $W_P$ has respective halves of the width Hp on both sides of the approximate line $L_S$ as the center line thereof, as shown in FIG. 26. In FIG. 26, symbols "o" (white circles) represents the data points corresponding to the first relationship between the cuff pressures $Pms_n$ and pulse amplitudes $Ams_n$ stored in the first memory 158.

A BP-change identifying means 172 identifies a change of the subject's blood pressure based on the first relationship (FIG. 24) between the cuff pressures $Pms_n$ and pulse amplitudes $Ams_n$ stored in the first memory 158 and the second relationship (FIG. 25) between the cuff pressures $Pmm_m$ and pulse amplitudes $Amm_m$ stored in the second memory 160. More specifically described, the BP-change identifying means 172 includes the first and second memories 158, 160, the pulse-amplitude and cuff-pressure window determining means 162, 168, and a deviation identifying means 174. The deviation identifying means 174 identifies a deviation of the second relationship from the first relationship based on the data points falling within the pulse-amplitude window $W_A$ out of the data points representing the pulse amplitudes $Amm_m$ (m=1 to k) and cuff pressures $Pmm_m$ (m=1 to k) stored in the second memory 160, and the data points falling within the cuff-pressure window $W_P$ out of the same data points. When the deviation identifying means 174 identifies a deviation between the first and second relationships, i.e., when the BP-change identifying means 172 identifies a change of the subject's blood pressure, the BP re-measuring device 72 immediately starts a BP measuring period to carry out a BP measurement on the subject. Thus, the output device 38 displays and/or records the subject's BP values measured upon identification of the BP change.

Next, there will be described the operation of the control device 26 of the second BP monitor by reference to the flow chart of FIG. 27 which represents the control program pre-stored in a ROM 32, and the flow chart of FIG. 28 which describes Step T9 of FIG. 27, i.e., abnormal BP-change identifying routine.

Figure 27:
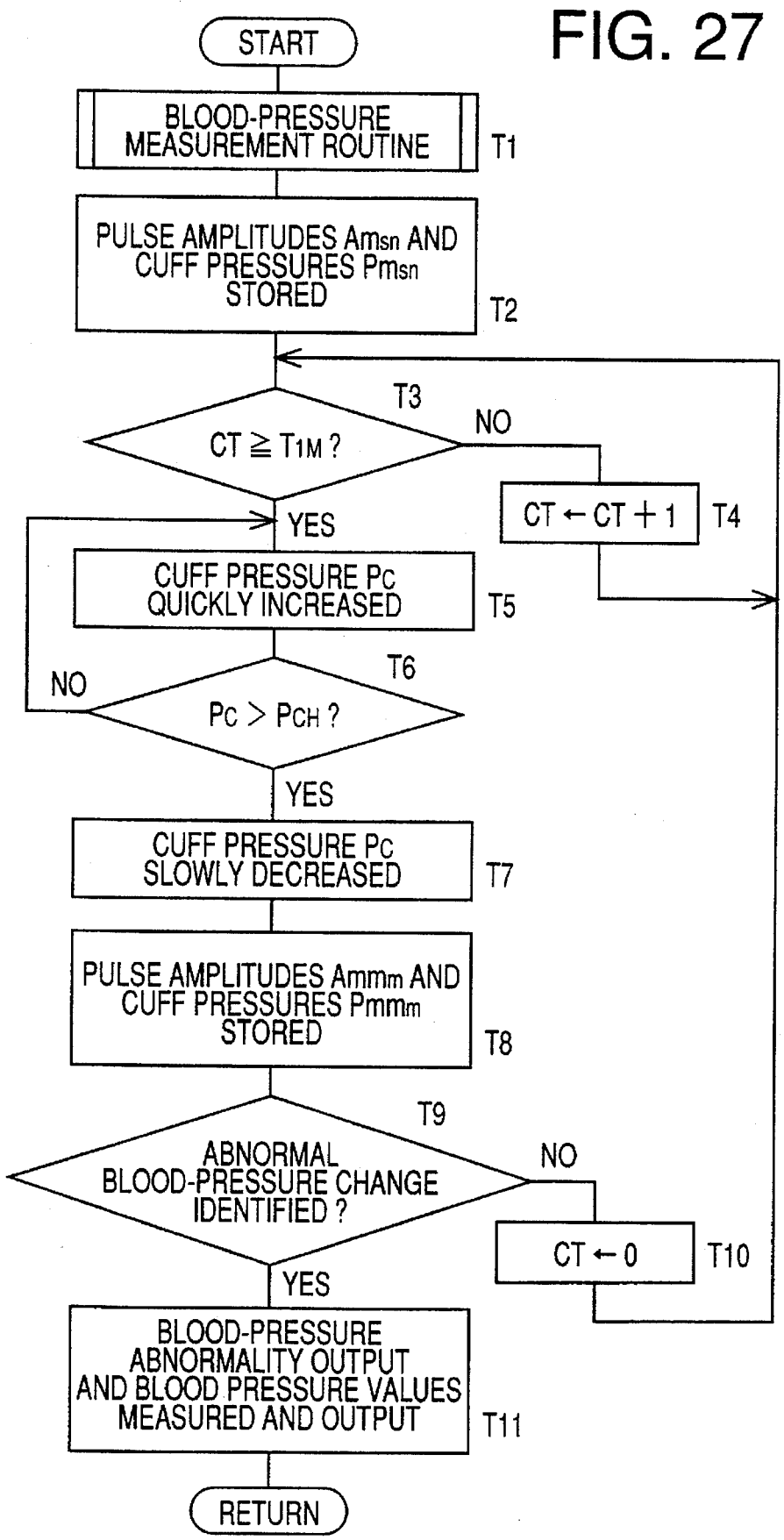
FIG. 27 is a flow chart corresponding to FIG. 4, which represents a control program according to which the control device of the second BP apparatus functions as illustrated in FIG. 23.
Figure 28:
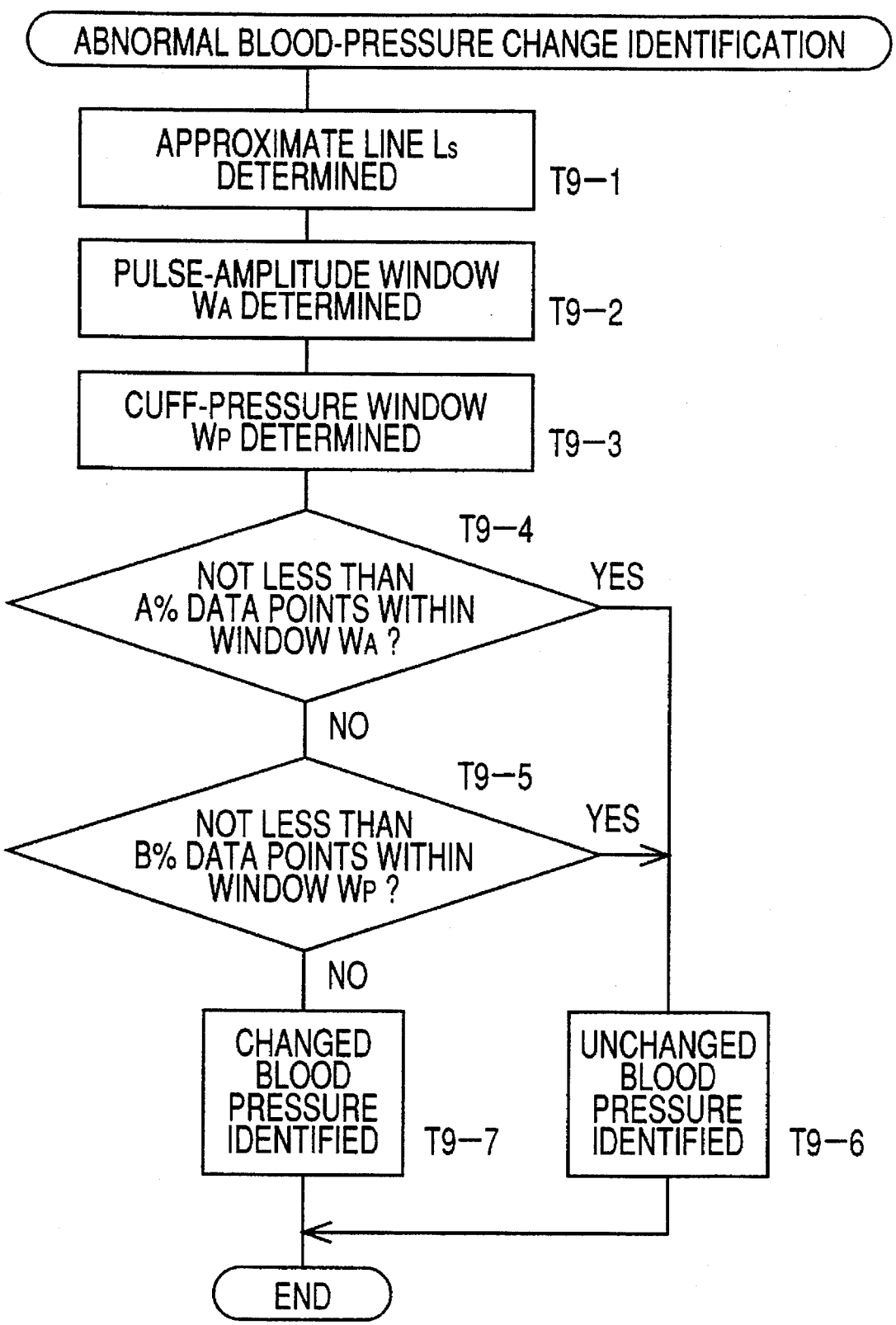
FIG. 28 is a flow chart representing an abnormal blood-pressure change identifying routine carried out at Step T9 of FIG. 27.

At steps not shown in FIG. 27, a CPU 28 of the control device 26 judges whether a start/stop switch 42 has been operated to start the second BP monitor, and judges whether a mode-selection switch 40 has been operated to select a continuous-monitor mode. If positive judgments are made in the two steps, the control of the CPU 28 carries out Step T1, i.e., BP measuring routine that provides part of the BP measuring device 54. At Step T1 corresponding to the initial BP-measuring period shown in FIG. 29, the pressing pressure Pc of the cuff 10 is quickly increased up to a target value $P_{CM}$ which is pre-determined to be higher than a systolic blood pressure of the subject and subsequently is slowly decreased at 2 to 3 mmHg/sec. A cuff pressure at which pulse amplitudes (FIG. 24) being detected largely increase during the slow decreasing of the cuff pressure Pc, is determined as a systolic blood pressure $P_{SYS}$ of the subject; a cuff pressure at which the pulse amplitudes largely decrease is determined as a diastolic blood pressure $P_{DIA}$ of the subject; and a cuff pressure at which the greatest pulse amplitude is detected is determined as a mean blood pressure $P_{MEAN}$ of the subject. After the blood pressure measurement is completed, the cuff pressure Pc is quickly decreased.

Subsequently, at Step T2, the respective amplitudes $Ams_n$ (n=1, 2, 3, . . . , j) of the heartbeat-synchronous pulses produced as pressure oscillations in the cuff 10 during the slow changing of the cuff pressure Pc in the above BP-measuring period, and the cuff pressures $Pms_n$ (n=1, 2, 3, . . . , j) at which the pulse amplitudes $Ams_n$ are respectively detected, are stored in an appropriate memory area of a RAM 30. FIG. 24 shows an example of a series of pulse amplitudes $Ams_n$ stored at Step T2. Thus, the appropriate memory area of the RAM 30 used at Step T2 corresponds to the first memory 158.

Step T2 is followed by Step T3 to judge whether a time or contents, CT, measured or counted by a time-signal counter provided in the microcomputer 26, has exceeded a predetermined time interval, $T_{1M}$. The counter CT starts to count the number of time-signals produced after a BP measurement ends at Step T1. The interval $T_{1M}$ is also the interval between each pair of successive BP-monitoring periods following the initial BP-measuring period. At the beginning, negative judgments are made at Step T3, so that the control of the CPU 28 goes to Step T4 to add "one" to the contents CT of the counter and then goes back to Step T3. Thus, Steps T3 and T4 are repeated.

Figure 29:
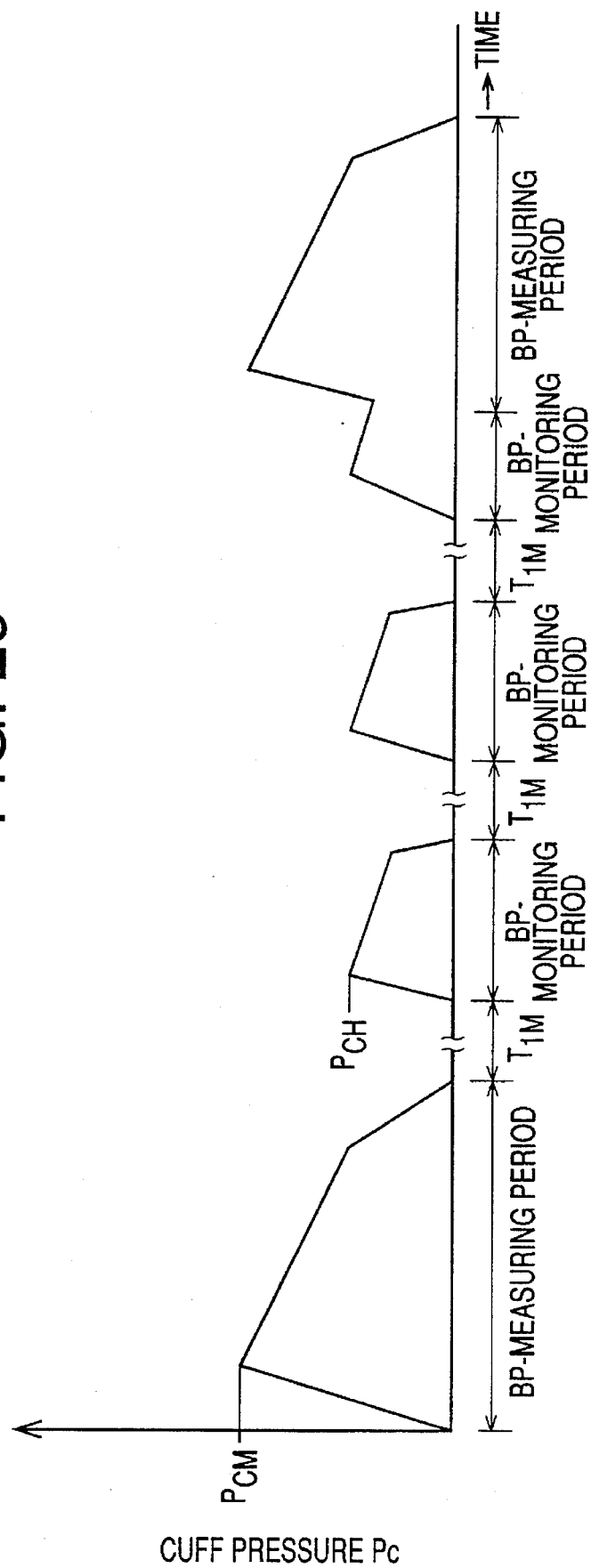
FIG. 29 is a time chart showing the time-wise change of cuff pressure Pc controlled by the control device of the apparatus of FIG. 23.

Meanwhile, if a positive judgment is made at Step T3, the control goes to Step T5 to start a first BP-monitoring period shown in FIG. 29, i.e., quickly increase the cuff pressure Pc up to a target value $P_{CH}$ which is pre-determined to be not higher than the measured mean blood pressure $P_{DIA}$ of the subject. At Step ST, the CPU 28 judges whether the cuff pressure Pc has been increased up to the target value $P_{CH}$. If a positive judgment is made at Step T6, the control goes to Step T7 to slowly decrease the cuff pressure Pc at 2 to 3 mmHg/sec as shown in FIG. 29.

At the following Step T8, the respective amplitudes $Amm_m$ (m=1, 2, 3, ..., k) of the heartbeat-synchronous pulses detected during the slow changing of the cuff pressure Pc in the above BP-monitoring period, and the cuff pressures $Pmm_m$ (m=1, 2, 3, ..., k) at which the pulse amplitudes $Amm_m$ are respectively detected, are stored in an appropriate memory area of the RAM 30. Thus, the appropriate memory area of the RAM 30 used at Step T8 corresponds to the second memory 160.

Step T8 is followed by Step T9, i.e., abnormal BP change identification routine corresponding to part of the BP-change identifying means 170. At Step T9, the CPU 28 judges whether the blood pressure of the subject has been changed abnormally. The abnormal BP-change identification routine of Step T9 will be described in detail by reference to the flow chart of FIG. 28.

First, at Step T9-1 corresponding to part of the approximate-line determining means 164, the CPU 28 determines an approximate line $L_S$ which approximates a portion of the first relationship stored in an appropriate memory area (i.e., first memory 158) of the RAM 30 which portion falls within a predetermined cuff-pressure range not higher than the subject's mean blood pressure $P_{MEAN}$, that is, range between the subject's diastolic blood pressure $P_{DIA}$ and the target pressure value $P_{CH}$. The approximate line $L_S$ approximates an envelope of the data points which represent the cuff pressures $Pms_n$ falling within the above cuff-pressure range and the corresponding pulse amplitudes $Ams_n$. The CPU 28 determines, as the approximate line $L_S$, a least-square approximate line or a regression line based on the above data points. The approximate line $L_S$ is employed as a center line of a pulse-amplitude window $W_A$.

At the following Step T9-2 corresponding to part of the pulse-amplitude window-width calculating means 166, the CPU 28 calculates a width $H_A$ of the pulse-amplitude window $W_A$ along the axis of ordinate indicative of the pulse amplitude, in such a manner that the upper and lower limits of the width or range $H_A$ are equal to ±30% of the approximate line $L_S$, respectively. The window $W_A$ has respective halves of the width $H_A$ on the upper and lower sides of the approximate line $L_S$ as the center line thereof as shown in FIG. 26. At the following Step T9-3 corresponding to part of the cuff-pressure window-width calculating means 168, the CPU 28 calculates a width, Hp, of a cuff-pressure window $W_P$ along the axis of abscissa indicative of the cuff pressure Pc, in such a manner that the upper (right-hand) and lower (left-hand) limits of the width or range Hp are equal to ±30% of the approximate line $L_S$, respectively. The window $W_P$ has respective halves of the width Hp on the left-hand and right-hand sides of the approximate line $L_S$ as the center line thereof as shown in FIG. 26. Broken lines representing the upper and lower limits of the width $H_A$, i.e., pulse-amplitude window $W_A$, are not parallel to the approximate line $L_S$, and similarly one-dot chain lines representing the upper and lower limits of the width Hp, i.e., cuff-pressure window $W_P$, are not parallel to the approximate line $L_S$.

Step T9-3 is followed by Step T9-4 to judge whether a proportion of the data points falling within the pulse-amplitude window $W_A$ out of the data points (indicated at symbols "□" (white quadrangles) in FIG. 26) representing the pulse amplitudes $Amm_m$ (m=1 to k) and cuff pressures $Pmm_m$ (m=1 to k) stored in the appropriate memory area (i.e., second memory 160) of the RAM 30, is not lower than a first reference value, A. At the following Step T9-5, the CPU 28 judges whether a proportion of the data points falling within the cuff-pressure window $W_P$ out of the same data points is not lower than a second reference value, B. The reference values A, B are employed to identify a change of the subject's blood pressure and each value may be predetermined at 50%. In the present embodiment, Steps T9-4 and T9-5 correspond to part of the deviation identifying means 174.

If a positive judgment is made at either one of Steps T9-4 and T9-5, the control of the CPU 28 goes to Step T9-6 to judge or identify that the subject's blood pressure remains unchanged. On the other hand, if a negative judgment is made at each of Steps T9-4 and T9-5, the control goes to Step T9-7 to judge that the subject's blood pressure has changed abnormally.

If at Step T9-6 the CPU 28 does not identify an abnormal BP change, a negative judgment is made at Step T9 of FIG. 27, so that the control goes to Step T10 to clear or reset the contents CT of the timer and then repeats Step T3 and the following steps. On the other hand, if a positive judgment is made at Step T9, the control goes to Step T11 to operate an output device 38 to inform the user of the identification of the abnormal BP change, and operates the BP re-measuring device 72 to immediately start a BP measuring period and carry out a BP measurement on the subject like at Step T1. This BP-measuring period is shown at the right-hand end of FIG. 29. Thus, the output device 38 displays and/or records the subject's BP values measured immediately after the identification of the abnormal BP change. Thus, Step T11 corresponds to part of the BP re-measuring device 72.

As is apparent from the foregoing description, in the second embodiment, the pulse amplitudes $Ams_n$ are detected as the pressure oscillations produced in the cuff 10 during the slowing decreasing of the cuff pressure Pc, in a BP measurement carried out at Step T1 corresponding to part of the BP measuring device 54, and the pulse amplitudes $Ams_n$ and the cuff pressures $Pms_n$ detected at the respective times of detection of the pulse amplitudes $Ams_n$ are stored in the first memory 158. In addition, the pulse amplitudes $Amm_m$ are detected during the slowing decreasing of the cuff pressure Pc from the predetermined value $P_{CH}$ not higher than the mean blood pressure $P_{MEAN}$ of the subject, in each of BP monitoring periods following a BP measurement of the BP-measuring device 54, and the pulse amplitudes $Amm_m$ and the cuff pressures $Pmm_m$ detected at the respective times of detection of the pulse amplitudes $Amm_m$ are stored in the second memory 160.

At Steps T9-1 and T9-2 corresponding to part of the pulse-amplitude window determining means 162, the pulse-amplitude window $W_A$ is determined based on the first relationship between the cuff pressures $Pms_n$ and pulse amplitudes $Ams_n$ stored in the first memory 158. At Steps T9-1 and T9-3 corresponding to part of the cuff-pressure window determining means 168, the cuff-pressure window $W_P$ is determined based on the first relationship between the cuff pressures $Pms_n$ and pulse amplitudes $Ams_n$ stored in the first memory 158. At Steps T9-4 and T9-5 corresponding to part of the deviation identifying means 174, whether the subject's blood pressure has changed or not is judged based on the data points falling within the pulse-amplitude window $W_A$ or cuff-pressure window $W_P$ out of all the data points representing the cuff pressures $Pmm_m$ and pulse amplitudes $Amm_m$ stored in the second memory 160.

The second BP monitor can monitor the blood pressure of the subject with high accuracy, because the apparatus identifies a change of the subject's blood pressure based on both the pulse amplitudes $Ams_n$ and cuff pressures $Pms_n$ obtained in a BP-measuring period and the pulse amplitudes $Amm_m$ and cuff pressures $Pmm_m$ obtained in a BP-monitoring period. In addition, since the BP monitor monitors the subject's blood pressure by iteratively changing the cuff pressure Pc within a low pressure range between the atmospheric pressure and the pre-determined pressure value $P_{CH}$ lower than the subject's mean blood pressure $P_{MEAN}$, the apparatus does not cause the subject to feel discomfort.

In the second embodiment, at Steps T9-4 and T9-5 corresponding to part of the deviation identifying means 174, the BP monitor identifies a change of the subject's blood pressure, when a proportion of the data points falling within the pulse-amplitude window $W_A$ is lower than the reference value A, and simultaneously when a proportion of the data points falling within the cuff-pressure window $W_P$ is lower than the reference value B. Thus, the present BP monitor can monitor the subject's blood pressure with higher reliability.

Moreover, in the second embodiment, the pulse-amplitude window determining means 162 or the cuff-pressure window determining means 168 includes an approximate-line determining means 164 for determining an approximate line $L_S$ which approximates a portion of the first relationship stored in the first memory 158 which portion falls within a predetermined cuff-pressure range lower than the pressure value $P_{CH}$ pre-determined to be not higher than the subject's mean blood pressure $P_{MEAN}$. The approximate-line determining means 164 determines, as the approximate line $L_S$, a least-square approximate line or a regression line based on the data points which represent the cuff pressures $Pms_n$ falling within the above cuff-pressure range and the corresponding pulse amplitudes $Ams_n$. The approximate line $L_S$ is employed as a center line of the pulse-amplitude window $W_A$ or cuff-pressure window $W_P$. Thus, the windows $W_A$, $W_P$ are determined with accuracy.

If an abnormal BP change is identified by the BP-change identifying means 172, the BP re-measuring device 72 immediately carries out a BP measurement using the cuff 10, and outputs the BP values obtained at the time of identification of the abnormal BP change. Thus, a medical worker such as a doctor or a nurse can quickly give appropriate treatments on a patient.

Next, there will be described a third embodiment of the present invention. The third embodiment also relates to a BP monitor and has the same hardware construction as that of the first embodiment shown in FIG. 1. However, the third BP monitor is operated according to a control program represented by the flow chart of FIG. 27 employed in the second embodiment, and the flow chart of FIG. 31, in place of the program represented by the flow charts of FIGS. 4 and 5 for the first embodiment.

Figure 30:
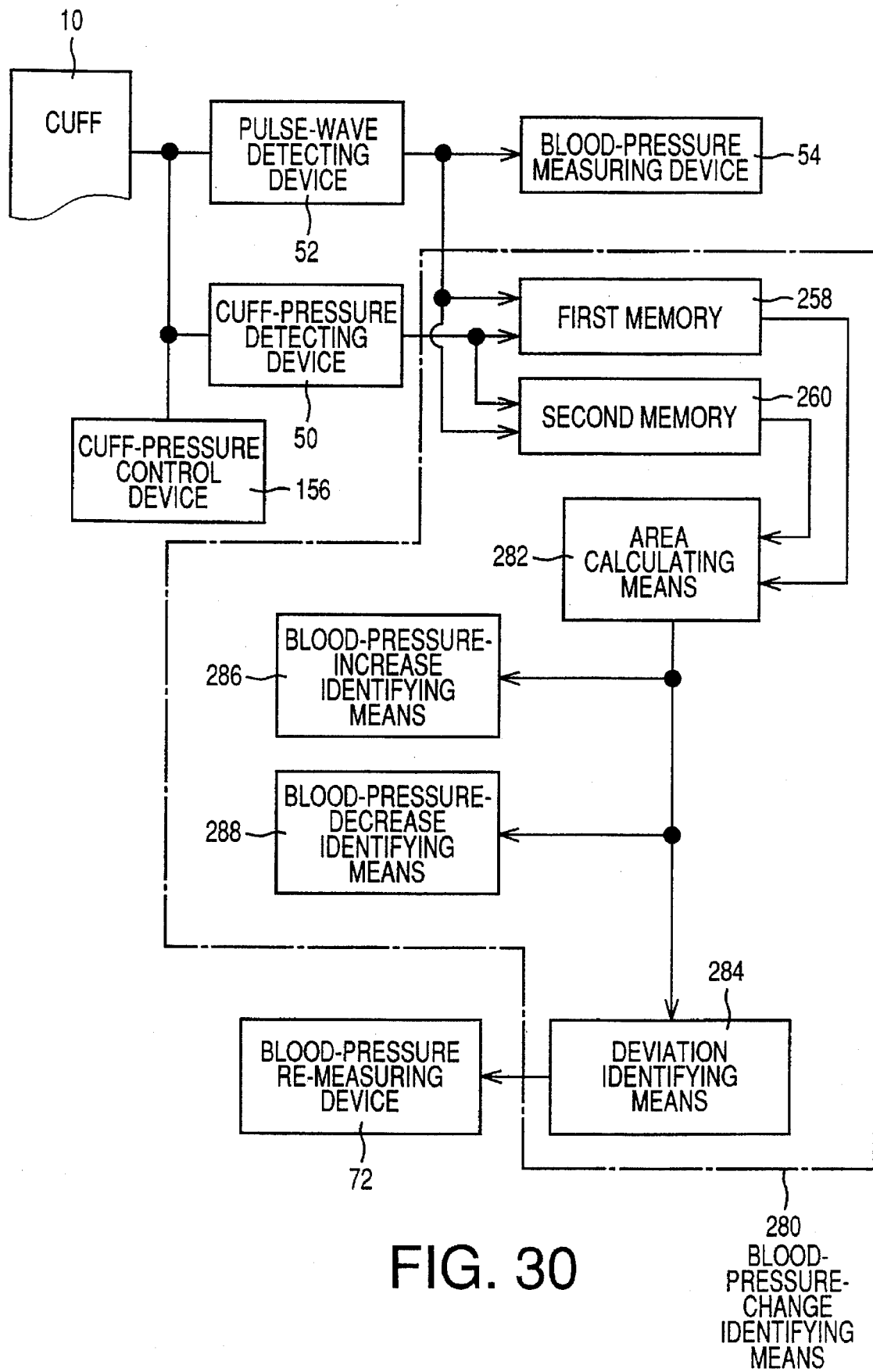
FIG. 30 is a diagrammatic view corresponding to FIG. 23, for illustrating various functions of a control device of yet another blood-pressure monitor apparatus as a third embodiment of the invention.

FIG. 30 shows various functions of a control device 26 of the third BP monitor. The third BP monitor includes an inflatable cuff 10, a cuff-pressure detecting device 50, a pulse-wave detecting device 52, an oscillometric BP measuring device 54, and a BP re-measuring device 72 all of which are the same as the counterparts of the first BP monitor shown in FIG. 2, and additionally includes a cuff-pressure control device 156 which is the same as the counterpart of the second BP monitor shown in FIG. 23.

A BP-change identifying means 280 identifies a change of subject's blood pressure based on a first relationship (FIG. 24) between cuff pressures $Pms_n$ and pulse amplitudes $Ams_n$ which are obtained in a BP-measuring period of the BP-measuring device 54 and are stored in a first memory 258 and based on a second relationship (FIG. 25) between cuff pressures $Pmm_m$ and pulse amplitudes $Amm_m$ which are obtained in a BP-monitoring period of the cuff-pressure control device 156 and are stored in a second memory 260. More specifically described, the BP-changing identifying means 280 includes the first and second memories 258, 260, an area calculating means 282, a deviation identifying means 284, a BP-increase identifying means 286, and a BP-decrease identifying means 288.

Figure 32:
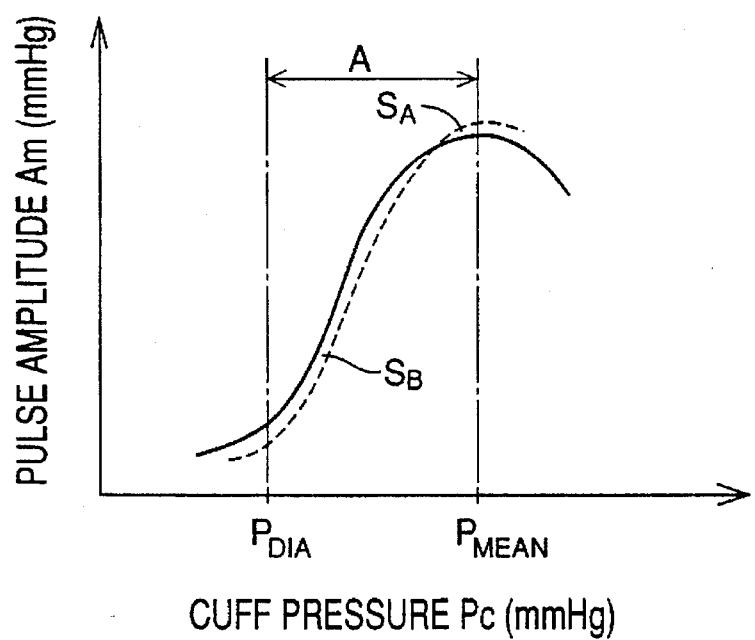
FIG. 32 is a graph showing a first curve (indicated at solid line) representing a first relationship between the pulse amplitudes and cuff pressures detected in a BP-measuring period, in comparison with a second curve (indicated at broken line) representing a second relationship between the pulse amplitudes and cuff pressures detected in a BP-monitoring period following the BP-measuring period, wherein the subject's blood pressure does not change.
Figure 33:
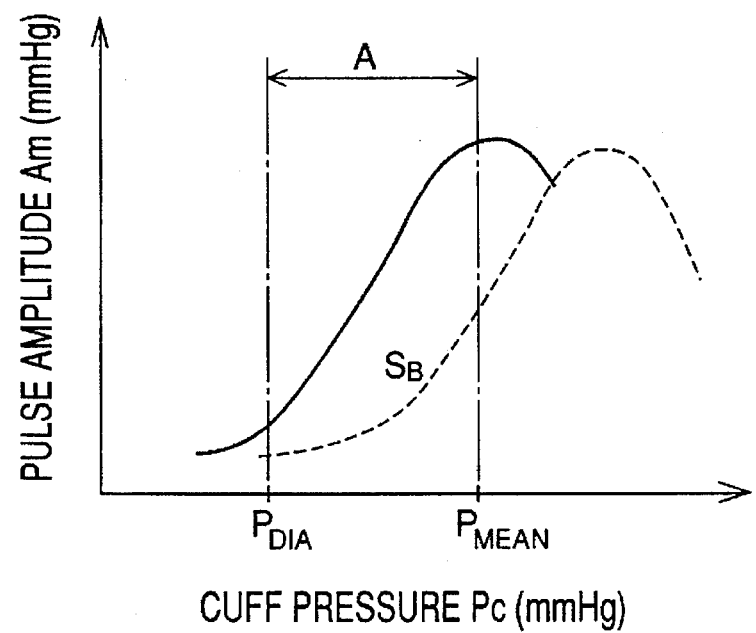
FIG. 33 a graph showing a first curve (indicated at solid line) representing a first relationship between the pulse amplitudes and cuff pressures detected in a BP-measuring period, in comparison with a second curve (indicated at broken line) representing a second relationship between the pulse amplitudes and cuff pressures detected in a BP-monitoring period, wherein the subject's blood pressure increases.
Figure 34:
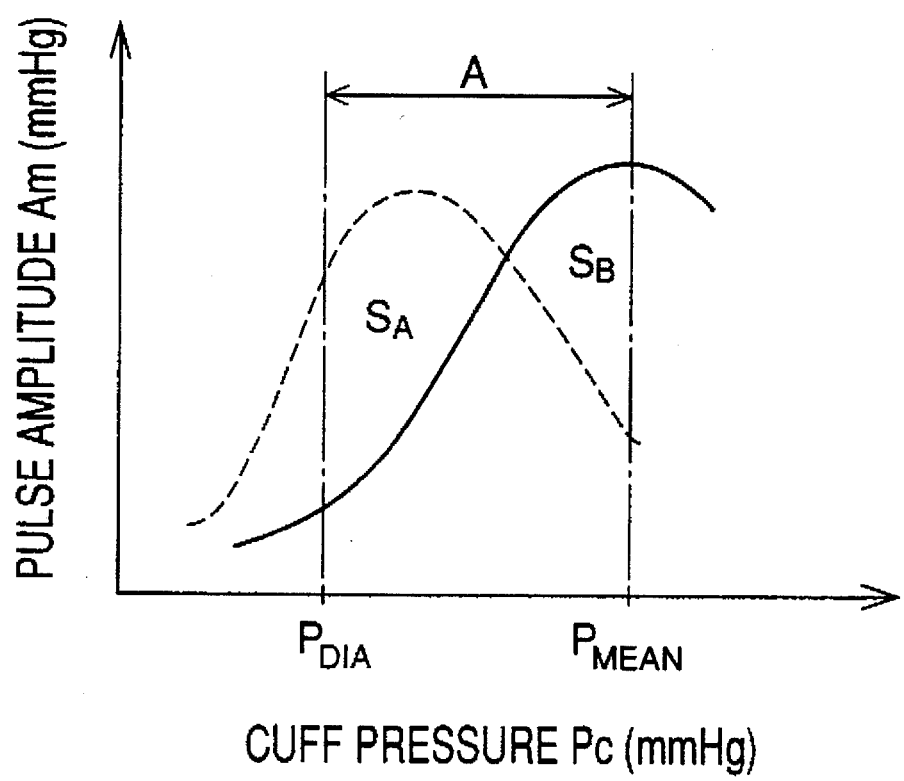
FIG. 34 is a graph showing a first curve (indicated at solid line) representing a first relationship between the pulse amplitudes and cuff pressures detected in a BP-measuring period, in comparison with a second curve (indicated at broken line) representing a second relationship between the pulse amplitudes and cuff pressures detected in a BP-monitoring period, wherein the subject's blood pressure decreases.
Figure 35:
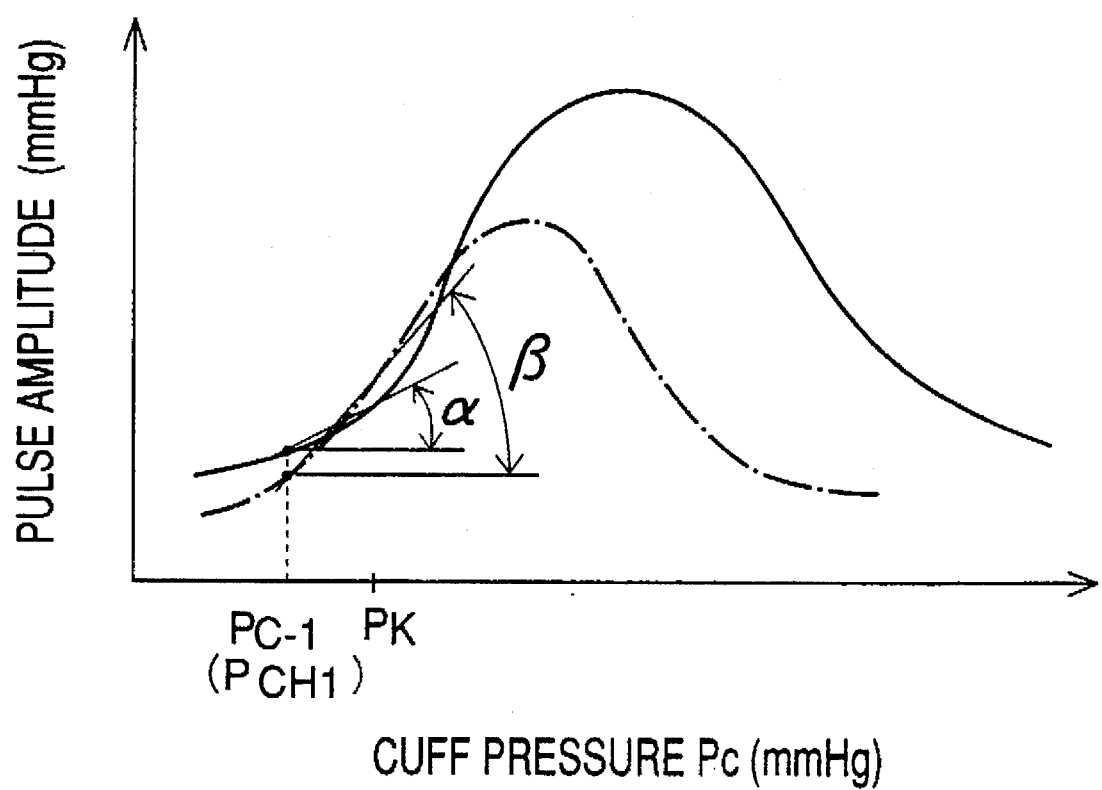
FIG. 35 is a view for illustrating a conventional manner in which the blood pressure of a living subject is monitored based on the pulse amplitudes obtained from an inflatable cuff wound around a body portion of the subject.

The area calculating means 282 calculates an area, S (=$S_A$+$S_B$), which is bounded by a first line representing the first relationship between the cuff pressures $Pms_n$ and pulse amplitudes $Ams_n$ stored in the first memory 258, and a second line representing the second relationship between the cuff pressures $Pmm_m$ and pulse amplitudes $Amm_m$ stored in the second memory 260, within a range, R, of the cuff pressure Pc which is predetermined to be not higher than subject's mean blood pressure $P_{MEAN}$ (e.g., range between subject's diastolic blood pressure $P_{DIA}$ and the target pressure value $P_{CH}$, or range between subject's diastolic and mean blood pressures $P_{DIA}$ and $P_{MEAN}$). The first line is a portion of an envelope of the pulse amplitudes $Ams_n$ which portion falls within the cuff-pressure range R, and the second line is a portion of an envelope of the pulse amplitudes $Ams_n$ which portion falls within the cuff-pressure range R. More specifically, the area calculating means 282 calculates a first area, $S_A$, which is bounded by a first portion of the first line and a first portion of the second line which is greater than the first portion of the first line with respect to the pulse amplitude, and a second area, $S_B$, which is bounded by a second portion of the first line and a second portion of the second line which is smaller than the second portion of the first line with respect to the pulse amplitude. In FIGS. 32, 33, and 34, the first line is indicated at solid line and the second line is indicated at broken line.

The deviation identifying means 284 identifies a deviation of the second relationship from the first relationship, based on the area S and the first and second areas $S_A$, $S_B$ each calculated by the area calculating means 282. The BP-change identifying means 280 identifies a change of the subject's blood pressure when the deviation identifying means 284 identifies the deviation of the second relationship from the first relationship. More specifically, the blood-pressure-increase identifying means 286 identifies an increase of the subject's blood pressure when the area S is not smaller than a reference value, $S_O$, and simultaneously when the first area $S_A$ is smaller than the second area $S_B$, and the blood-pressure-decrease identifying means 288 identifies a decrease of the subject's blood pressure when the area S is not smaller than the reference value $S_O$ and simultaneously when the first area $S_A$ is not smaller than the second area $S_B$.

Figure 31:
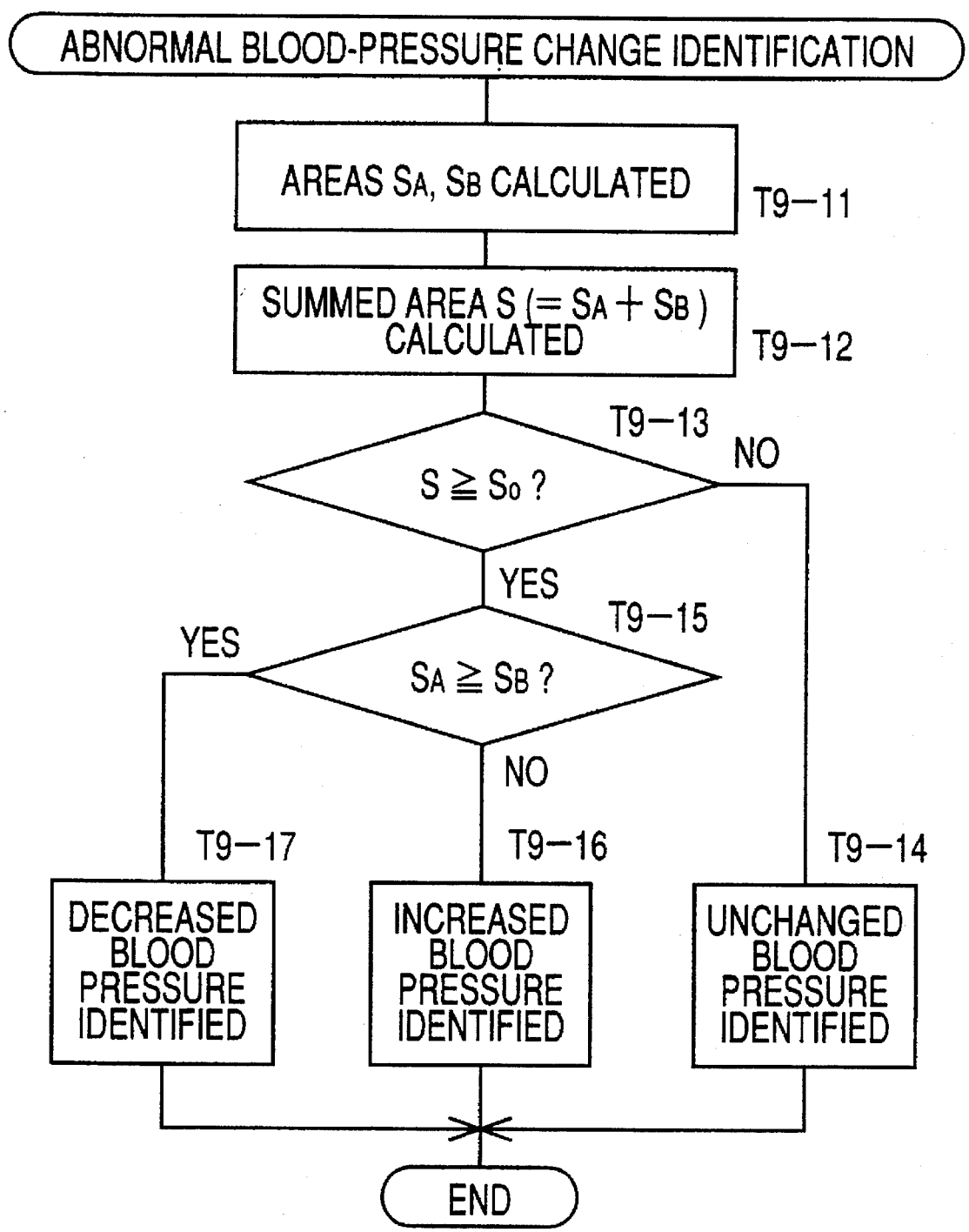
FIG. 31 is a flow chart corresponding to FIG. 28, which represents a control program according to which the control device of the third BP apparatus functions as illustrated in FIG. 30.

FIG. 31 shows an abnormal BP change identifying routine which is carried out at Step T9 of the flow chart of FIG. 27 by a control device 26 of the third BP monitor. At Step T9-11, a CPU 28 of the control device 26 calculates the first and second areas $S_A$, $S_B$ based on the data stored in the first and second memories 258, 260. At Step T9-12, the CPU 28 adds the first and second areas $S_A$, $S_B$ to each other, thereby providing the area S (=$S_{A+SB}$) which is bounded by the first line representing the first relationship between the cuff pressures $Pms_n$ and pulse amplitudes $Ams_n$ stored in the first memory 258 and the second line representing the second relationship between the cuff pressures $Pmm_m$ and pulse amplitudes $Amm_m$ stored in the second memory 260, within the cuff-pressure range R pre-determined to be not higher than the subject's mean blood pressure $P_{MEAN}$. In the present embodiment, Steps T9-11 and T9-12 correspond to part of the area calculating means 282.

At Step T9-13 corresponding to part of the deviation identifying means 284, the CPU 28 judges whether the area S is not smaller than the reference value $S_O$ which is pre-determined based on experimental results to identify an abnormal change of human beings' blood pressure. If a negative judgment is made at Step T9-13, the control of the CPU 28 goes to Step T9-14 and judges that the subject's blood pressure has not changed. FIG. 32 shows the case where the deviation of the second line indicated at broken line from the first line indicated at solid line is small in a normal range.

On the other hand, if a positive judgment is made at Step T9-13, the control of the CPU 28 goes to Step T9-15 to judge whether the first area $S_A$ is not smaller than the second area $S_B$. If a negative judgment is made at Step T9-15, the control goes to Step T9-16 corresponding to part of the BP-increase identifying means 286 and judges that the subject's blood pressure has increased abnormally. FIG. 33 shows the case where the second line is largely deviated from the first line and the second area $S_B$ is greater than the first area $S_A$. On the other hand, if a positive judgment is made at Step T9-15, the control goes to Step T9-17 corresponding to part of the BP-decrease identifying means 288 and judges that the subject's blood pressure has decreased abnormally. FIG. 34 shows the case where the second line is largely deviated from the first line and the first area $S_A$ is greater than the second area $S_B$.

As is apparent from the foregoing description, in the third embodiment, the pulse amplitudes $Ams_n$ are detected as the pressure oscillations produced in the cuff 10 during the slow decreasing of the cuff pressure Pc, in a BP-measuring period of the BP measuring device 54, and the pulse amplitudes $Ams_n$ and the cuff pressures $Pms_n$ detected at the respective times of detection of the pulse amplitudes $Ams_n$ are stored in the first memory 258. In addition, the pulse amplitudes $Amm_m$ are detected during the slow decreasing of the cuff pressure Pc from the predetermined value $P_{CH}$ not higher than the mean blood pressure $P_{MEAN}$ of the subject, in each of BP monitoring periods following a BP measurement of the BP-measuring device 54, and the pulse amplitudes $Amm_m$ and the cuff pressures $Pmm_m$ detected at the respective times of detection of the pulse amplitudes $Amm_m$ are stored in the second memory 260. The area calculating means 282 calculates the area S which is bounded by the first line representing the first relationship between the cuff pressures $Pms_n$ and pulse amplitudes $Ams_n$ stored in the first memory 258, and the second line representing the second relationship between the cuff pressures $Pmm_m$ and pulse amplitudes $Amm_m$ stored in the second memory 260, within the predetermined cuff-pressure range R. The deviation identifying means 284 identifies a deviation of the second relationship from the first relationship, based on the area S calculated by the area calculating means 282.

The third BP monitor can monitor the blood pressure of the subject with high accuracy, because the apparatus identifies a change of the subject's blood pressure based on the area S, i.e., based on both the pulse amplitudes $Ams_n$ and cuff pressures $Pms_n$ obtained in a BP-measuring period and the pulse amplitudes $Amm_m$ and cuff pressures $Pmm_m$ obtained in a BP-monitoring period. In addition, since the BP monitor monitors the subject's blood pressure by iteratively changing the cuff pressure Pc within a low pressure range between the atmospheric pressure and the predetermined pressure value $P_{CH}$ lower than the subject's mean blood pressure $P_{MEAN}$, the apparatus does not cause the subject to feel discomfort.

In the third embodiment, the area calculating means 282 calculates the first area $S_A$ which is bounded by the first portion of the first line and the first portion of the second line greater than the first portion of the first line with respect to the pulse amplitude, and the second area $S_B$ which is bounded by the second portion of the first line and the second portion of the second line smaller than the second portion of the first line with respect to the pulse amplitude. The blood-pressure-increase identifying means 286 identifies an increase of the subject's blood pressure when the area S is not smaller than the reference value $S_O$ and simultaneously when the first area $S_A$ is smaller than the second area $S_B$, and the blood-pressure-decrease identifying means 288 identifies a decrease of the subject's blood pressure when the area S is not smaller than the reference value $S_O$ and simultaneously when the first area $S_A$ is not smaller than the second area $S_B$. Thus, the third BP monitor can monitor the blood pressure of the subject with higher accuracy.

While the present invention has been described in its preferred embodiments, the invention may otherwise be embodied.

For example, in each of the first to third embodiments, the BP monitor may be modified such that the control device 26 repeats Steps S1 to S11 or Steps T1 to T11 at a regular interval of time such as 30 minutes or 1 hour.

In addition, Step S11 or T11 may be modified such that only the output device 38 outputs an abnormality of the subject's blood pressure. In the latter case, the BP remeasuring device 72 is omitted.

In each of the illustrated embodiments, when the cuff pressure Pc is slowly decreased by the cuff-pressure control device 56, 156, the BP monitor determines the BP values of the subject and collects the pulse amplitudes and cuff pressures. However, it is possible that when the cuff pressure Pc is slowly increased, the BP monitor determine the BP values of the subject and collect the pulse amplitudes and cuff pressures.

In the first embodiment, the first and second pulse-rate determining means 66, 68 determine, at Steps S2 and S8, the pulse rates $PR_s$, $PR_m$ based on the pulses detected as the pressure oscillations produced in the cuff used for the BP measurements. However, it is possible to employ an exclusive pulse-wave sensor or electrocardiograph sensor which obtains a photoelectric pulse wave, a volumetric pulse wave, an impedance pulse wave, or an electrocardiograph signal, from a living subject. In the latter case, the pulse rates $PR_s$, $PR_m$ are determined based on the output signal of the exclusive sensor.

In the second and third embodiments, an abnormal change of subject's blood pressure is identified based on the proportion of the data points which fall within each of the pulse-amplitude and cuff-pressure windows $W_A$, $W_P$ determined based on the first relationship, with respect to all the data points representing the second relationship, or based on the area S which is bounded by the first and second lines respectively representing the first and second relationships, within the predetermined cuff-pressure range A. However, it is possible that an abnormal change of subject's blood pressure be identified based on a coefficient of correlation between the first and second relationships. In the latter case, too, a change of subject's blood pressure is identified based on a deviation of the second relationship from the first relationship.

In the second embodiment, the pulse-amplitude and cuff-pressure windows $W_A$, $W_P$ are defined as having, as the center line thereof, the linear approximate line $L_S$ approximating the first relationship stored in the first memory 158.

However, it is possible that one or each of the windows $W_A$, $W_P$ be defined as having, as a reference line thereof, a curved envelope of the pulse amplitudes $Ams_n$ stored in the first memory 158, or a polygonal line connecting the data points representing the cuff pressures $Pms_n$ and pulse amplitudes $Ams_n$ stored in the same memory 158.

While in the second and third embodiments the cuff pressure Pc is increased, in each BP-monitoring period, up to the target value $P_{CH}$ which is predetermined to be slightly lower than the subject's mean blood pressure $P_{MEAN}$, a different target value $P_{CH}$ may be employed which is predetermined to be slightly higher than the subject's diastolic blood pressure $P_{DIA}$.

While in the third embodiment the cuff-pressure range R between the subject's diastolic and mean blood pressures $P_{DIA}$ and $P_{MEAN}$ is used to calculate the area S, a different cuff-pressure range R may be employed. For example, in the case where the target pressure value $P_{CH}$ is predetermined to be slightly lower than the mean blood pressure $P_{MEAN}$, a cuff-pressure range R' between the diastolic blood pressure $P_{DIA}$ and the target pressure value $P_{CH}$, or a range R' smaller than the range R' by an appropriate amount may be used.

It is to be understood that the present invention may be embodied with other changes, improvements, and modifications that may occur to those skilled in the art without departing from the scope and spirit of the invention defined in the appended claims.

What is claimed is:

1. A blood pressure monitor apparatus for monitoring a blood pressure of a living subject, comprising:

an inflatable cuff adapted to be wound around a body portion of a living subject;

a blood-pressure measuring device in fluid communication with said cuff which changes a pressing pressure of said cuff in a first pressure range whose upper limit is not lower than a systolic blood pressure of the subject and obtains a first plurality of heartbeat-synchronous pulses from the cuff while the pressure of the cuff is changed in said first pressure range;

a cuff-pressure control device in fluid communication with said cuff which iteratively changes, after a predetermined rest period following the blood pressure measurement of said blood-pressure measuring device, the pressure of said cuff in a second pressure range whose upper limit is a predetermined value lower than the systolic blood pressure of the subject and obtains a second plurality of heartbeat-synchronous pulses from the cuff while the pressure of the cuff is changed in said second pressure range; and blood-pressure-change identifying means for identifying a change of the blood pressure of the subject based on (a) respective amplitudes of said first plurality of heartbeat-synchronous pulses obtained from said cuff during said blood pressure measurement of said blood-pressure measuring device, (b) respective pressures of said cuff when said first plurality of pulses are obtained, (c) respective amplitudes of said second plurality of heartbeat-synchronous pulses obtained from said cuff during each of the iterative changes of the cuff pressure by said cuff-pressure control device, and (d) respective pressures of said cuff when said second plurality of pulses are obtained.

2. A blood pressure monitor apparatus according to claim 1, further comprising:

a first memory which stores the respective amplitudes of said first pulses obtained from said cuff during said blood pressure measurement of said blood-pressure measuring device, and the respective pressures of said cuff when said first pulses are obtained; and a second memory which stores the respective amplitudes of said second pulses obtained from said cuff during said each of the iterative changes, of the cuff pressure by said cuff-pressure control device, and the respective pressures of said cuff when said second pulses are obtained.

3. A blood pressure monitor apparatus according to claim 1, wherein said blood-pressure-change identifying means comprises:

cuff-pressure comparing means for comparing a first pressure of said cuff at which one of said first plurality of pulses which has a greatest amplitude of the first plurality of pulses obtained when the pressures of the cuff are not higher than said predetermined value is obtained with a second pressure of said cuff at which one of said second plurality of pulses which has a greatest amplitude is obtained for providing a comparison result; and means for identifying said change of the blood pressure of the subject when said a comparison result indicates that said second cuff pressure is lower than said first cuff pressure.

4. A blood pressure monitor apparatus according to claim 1, wherein said blood-pressure-change identifying means comprises:

cuff-pressure comparing means for comparing a first pressure of said cuff at which one of said first plurality of pulses which has a greatest amplitude of the first plurality of pulses obtained when the pressures of the cuff are not higher than said predetermined value is obtained with a second pressure of said cuff at which one of said second plurality of pulses which has a greatest amplitude is obtained; and for providing a comparison result judging means for judging, when said comparison result indicates that said second cuff pressure is not lower than said first cuff pressure, whether an amplitude of said second plurality of pulses which corresponds to a reference cuff-pressure value has changed from an amplitude of said first plurality pulses which corresponds to said reference cuff-pressure value, by not smaller than a predetermined proportion of said amplitude of said first plurality of pulses; and means for identifying said change of the blood pressure of the subject when said judging means makes a positive judgment.

5. A blood pressure monitor apparatus according to claim 4, wherein said amplitude of said second plurality of pulses is a value of an envelope or a cumulative curve of the second plurality of pulses and said amplitude of said first plurality of pulses is a value of an envelope or a cumulative curve of the first plurality of pulses.

6. A blood pressure monitor apparatus according to claim 1, wherein said blood-pressure-change identifying means comprises:

rate-of-change calculating means for calculating a first rate of change of the respective amplitudes of the first plurality of pulses obtained when the pressures of the cuff are not higher than the predetermined value, with respect to the corresponding pressures of said cuff, and a second rate of change of said respective amplitudes of said second plurality of pulses with respect to said respective pressures of said cuff when said second plurality of pulses are obtained; and means for identifying said change of the blood pressure of the subject when a difference between said first and second rates of change is greater than a second predetermined value.

7. A blood pressure monitor apparatus according to claim 1, further comprising:

a first pulse-rate measuring device which measures a first pulse rate of the subject during the blood pressure measurement of said blood-pressure measuring device; and a second pulse-rate measuring device which measures a second pulse rate of the subject during each of the iterative changes of the cuff pressure by said cuff-pressure control device, said blood-pressure-change identifying means identifying said change of the blood pressure of the subject when said second pulse rate has changed from said first pulse rate by not smaller than a predetermined amount.

8. A blood pressure monitor apparatus according to claim 1, wherein said cuff-pressure control device comprises means for iteratively changing, after said predetermined rest period, the pressure of said cuff in said second pressure range whose upper limit is said predetermined value not higher than a mean blood pressure of the subject, and wherein s aid blood-pressure-change identifying means comprises means for identifying said change of the blood pressure of the subject based on a first relationship between said respective amplitudes of said first plurality of pulses and said respective pressures of said cuff when said first plurality of pulses are obtained and a second relationship between said respective amplitudes of said second plurality of pulses and said respective pressures of said cuff when said second plurality of pulses are obtained.

9. A blood pressure monitor apparatus according to claim 8, wherein said blood-pressure-change identifying means comprises:

pulse-amplitude-window determining means for determining, in a coordinate system defined by a first axis indicative of the cuff pressure and a second axis indicative of the pulse amplitude, a pulse-amplitude window which is defined by a reference line representing said first relationship and has a first width along said second axis;

deviation identifying means for counting, from data points plotted in said coordinate system which points represent, as said second relationship, said respective amplitudes of said second plurality of pulses and said respective pressures of said cuff when said second plurality of pulses are obtained, a first number of the data points which fall within said pulse-amplitude window, and identifying a deviation of said second relationship from said first relationship based on the counted first number; and means for identifying said change of the blood pressure of the subject when said deviation identifying means identifies said deviation of said second relationship from said first relationship.

10. A blood pressure monitor apparatus according to claim 9, wherein said blood-pressure-change identifying means further comprises cuff-pressure window determining means for determining, in said coordinate system, a cuff-pressure window which is defined by said reference line and has a second width along said first axis, said deviation identifying means counting, from said data points plotted in said coordinate system, a second number of the data points which fall within said cuff-pressure window, and identifying a deviation of said second relationship from said first relationship based on both said counted first number and the counted second number, said blood-pressure-change identifying means comprising means for identifying said change of the blood pressure of the subject when-said deviation identifying means identifies said deviation of said second relationship from said first relationship based on both said first and second counted numbers.

11. A blood pressure monitor apparatus according to claim 9, wherein said pulse-amplitude window determining means comprises:

approximate-line determining means for determining, as said reference line, an approximate line approximating said first relationship within a range of the pressures of said cuff which are not higher than said mean blood pressure of the subject; and means for determining said pulse-amplitude window which has said approximate line as a center line thereof and respective halves of said first width on both sides of said approximate line.

12. A blood pressure monitor apparatus according to claim 11, wherein said approximate-line determining means comprises means for determining, as said approximate line, one of (a) a least-square approximate line and (b) a regression line, based on data points plotted in said coordinate system which points represent, as said first relationship, said respective amplitudes of said first plurality of pulses and said respective pressures of said cuff when said first plurality of pulses are obtained.

13. A blood pressure monitor apparatus according to claim 10, wherein said cuff-pressure window determining means comprises:

approximate-line determining means for determining, as said reference line, an approximate line approximating said first relationship within a range of the pressures of said cuff which are not higher than said mean blood pressure of the subject; and means for determining said cuff-pressure window which has said approximate line as a center line thereof and respective halves of said second width on both sides of said approximate line.

14. A blood pressure monitor apparatus according to claim 13, wherein said approximate-line determining means comprises means for determining, as said approximate line, one of (a) a least-square approximate line and (b) a regression line, based on data points plotted in said coordinate system which points represent, as said first relationship, said respective amplitudes of said first plurality of pulses and said respective pressures of said cuff when said first plurality pulses are obtained.

15. A blood pressure monitor apparatus according to claim 8, wherein said blood-pressure-change identifying means comprises:

area calculating means for calculating an area bounded by a first line representing said first relationship and a second line representing said second relationship, within a predetermined range of the pressures of said cuff;

deviation identifying means for identifying a deviation of said second relationship from said first relationship based on the calculated area; and means for identifying said change of the blood pressure of the subject when said deviation identifying means identifies said deviation of said second relationship from said first relationship.

16. A blood pressure monitor apparatus according to claim 15, wherein said area calculating means comprises means for calculating a first area bounded by a first portion of said first line and a first portion of said second line which is greater than said first portion of said first line with respect to the pulse amplitude, and a second area bounded by a second portion of said first line and a second portion of said second line which is smaller than said second portion of said first line with respect to the pulse amplitude, and wherein said blood-pressure-change identifying means comprises means for identifying a decrease of the blood pressure of the subject when said first area is greater than said second area.

17. A blood pressure monitor apparatus according to claim 15, wherein said area calculating means comprises means for calculating a first area bounded by a first portion of said first line and a first portion of said second line which is greater than said first portion of said first line with respect to the pulse amplitude, and a second area bounded by a second portion of said first line and a second portion of said second line which is smaller than said second portion of said first line with respect to the pulse amplitude, and wherein said blood-pressure-change identifying means comprises means for identifying an increase of the blood pressure of the subject when said second area is greater than said first area.

18. A blood pressure monitor apparatus according to claim 1, further comprising a pulse-wave detector which detects, as a pressure change produced in said cuff, an amplitude of each of said first and second plurality of pulses.

19. A blood pressure monitor apparatus according to claim 18, further comprising a cuff-pressure detector which detects the pressing pressure of said cuff when said each of said first and second plurality of pulses is detected by said pulse-wave detector.

20. A blood pressure monitor apparatus according to claim 1, further comprising an output device which informs a user of occurrence of an abnormal blood-pressure change when said blood-pressure-change identifying means identifies said change of the blood pressure of the subject.

21. A blood pressure monitor apparatus according to claim 1, further comprising a blood-pressure re-measuring device which substantially immediately measures a new blood pressure of the subject when said blood-pressure-change identifying means identifies said change of the blood pressure of the subject.

* * * * *